US012019075B2

(12) United States Patent
Heeren et al.

(10) Patent No.: US 12,019,075 B2
(45) Date of Patent: Jun. 25, 2024

(54) ZWITTERIONIC NANOPARTICLES

(71) Applicants: FRAUNHOFER-GESELLSCHAFT ZUR FOERDERUNG DER ANGEWANDTEN FORSCHUNG E. V., Munich (DE); UNIVERSITAETSKLINIKUM HAMBURG-EPPENDORF, Hamburg (DE)

(72) Inventors: Joerg Heeren, Hamburg (DE); Alexander Fischer, Ahrensburg (DE); Theo Schotten, Hamburg (DE); Michaela Steuter, Hamburg (DE); Jan-Philip Merkl, Hamburg (DE); Horst Weller, Hamburg (DE)

(73) Assignees: FRAUNHOFER-GESELLSCHAFT ZUR FOERDERUNG DER ANGEWANDTEN FORSCHUNG E. V., Munich (DE); UNIVERSITAETSKLINIKUM HAMBURG-EPPENDORF, Hamburg (DE)

( * ) Notice: Subject to any disclaimer, the term of this patent is extended or adjusted under 35 U.S.C. 154(b) by 445 days.

(21) Appl. No.: 16/479,576

(22) PCT Filed: Jan. 19, 2018

(86) PCT No.: PCT/EP2018/051288

§ 371 (c)(1),
(2) Date: Jul. 19, 2019

(87) PCT Pub. No.: WO2018/134344

PCT Pub. Date: Jul. 26, 2018

(65) Prior Publication Data

US 2019/0367807 A1 Dec. 5, 2019

(30) Foreign Application Priority Data

Jan. 20, 2017 (DE) .................... 10 2017 101 057.2

(51) Int. Cl.

| | |
|---|---|
| ***G01N 33/58*** | (2006.01) |
| ***A61K 9/51*** | (2006.01) |
| ***A61P 29/00*** | (2006.01) |
| ***A61P 37/06*** | (2006.01) |
| ***C09K 11/02*** | (2006.01) |
| ***C09K 11/06*** | (2006.01) |
| ***C09K 11/08*** | (2006.01) |
| *B82Y 15/00* | (2011.01) |

(52) U.S. Cl.

CPC .......... *G01N 33/588* (2013.01); *A61K 9/5115* (2013.01); *A61P 29/00* (2018.01); *A61P 37/06* (2018.01); *C09K 11/025* (2013.01); *C09K 11/06* (2013.01); *C09K 11/08* (2013.01); *G01N 33/587* (2013.01); *B82Y 15/00* (2013.01); *C09K 2211/10* (2013.01)

(58) Field of Classification Search

CPC .. G01N 33/588; G01N 33/587; A61K 9/5115; A61P 29/00; A61P 37/06; C09K 11/025; C09K 11/06; C09K 11/08; C09K 2211/10; B82Y 15/00

See application file for complete search history.

(56) References Cited

U.S. PATENT DOCUMENTS

| | | | | |
|---|---|---|---|---|
| 8,182,789 | B2 | 5/2012 | Tisato et al. | |
| 10,130,716 | B2 * | 11/2018 | Jiang | A61K 47/58 |
| 2010/0258789 | A1 | 10/2010 | Akai et al. | |
| 2010/0316797 | A1 | 12/2010 | Ying et al. | |
| 2012/0052513 | A1 | 3/2012 | Thalappil et al. | |
| 2014/0235803 | A1 | 8/2014 | Jiang et al. | |

FOREIGN PATENT DOCUMENTS

| | | |
|---|---|---|
| WO | 2013090601 A2 | 6/2013 |

OTHER PUBLICATIONS

Kamimoto, M. et al., "Uptake ability of hepatic sinusoidal endothelial cells and enhancement by lipopolysaccharide," Biomedical Research, vol. 26, No. 3, Jun. 2005, 9 pages.

Azzouz, R. et al., "Selective Tetrahydropyranylation under Non-Acidic Conditions," Synlett, vol. 37, No. 18, Nov. 3, 2005, Available Online Oct. 10, 2005, 3 pages.

Schipper, M. et al., "Particle Size, Surface Coating, and PEGylation Influence the Biodistribution of Quantum Dots in Living Mice," Small, vol. 5, No. 1, Jan. 2009, 18 pages.

Muro, E. et al., "Small and Stable Sulfobetaine Zwitterionic Quantum Dots for Functional Live-Cell Imaging," Journal of the American Chemical Society, vol. 132, No. 13, Apr. 7, 2010, Available Online Mar. 17, 2010, 2 pages.

Petros, R. et al., "Strategies in the design of nanoparticles for therapeutic applications," Nature Reviews: Drug Discovery, vol. 9, No. 8, Aug. 2010, Available Online Jul. 9, 2010, 13 pages.

Longmire, M. et al., "Biologically optimized nano-sized molecules and particles: more than just size," Bioconjugate Chemistry, vol. 22, No. 6, Jun. 15, 2011, Available Online May 11, 2011, 15 pages.

Sørensen, K. et al., "The scavenger endothelial cell: a new player in homeostasis and immunity," American Journal of Physiology: Regulatory, Integrative and Comparative Physiology, vol. 303, No. 12, Dec. 15, 2012, Available Online Oct. 17, 2012, 14 pages.

(Continued)

*Primary Examiner* — Robert S Cabral
(74) *Attorney, Agent, or Firm* — McCoy Russell LLP

(57) ABSTRACT

The present invention relates to a zwitterionic nanoparticle, the zwitterionic nanoparticle comprising at least one nanoparticle and a zwitterionic case enclosing the nanoparticle. Furthermore, the present invention relates to a composition, a method of binding a zwitterionic nanoparticle and the use of a zwitterionic nanoparticle.

17 Claims, 7 Drawing Sheets

(56) References Cited

OTHER PUBLICATIONS

Carambia, A. et al., "TGF-β-dependent induction of CD4+CD25+ Foxp3+ Tregs by liver sinusoidal endothelial cells," Journal of Hepatology, vol. 61, No. 3, Sep. 2014, Available Online May 2, 2014, 6 pages.
Carambia, A. et al., "Nanoparticle-based autoantigen delivery to Treg-inducing liver sinusoidal endothelial cells enables control of autoimmunity in mice," Journal of Hepatology, vol. 62, No. 6, Jun. 2015, Available Online Jan. 21, 2015, 8 pages.
ISA European Patent Office, International Search Report Issued in Application No. PCT/EP2018/051288, dated Apr. 18, 2018, WIPO, 6 pages.
Illum, L. et al., "Blood clearance and organ deposition of intravenously administered colloidal particles. The effects of particle size, nature and shape," International Journal of Pharmaceutics, vol. 12, No. 2-3, Oct. 1982, 12 pages.
Baughman, T. et al., "The facile preparation of alkenyl metathesis synthons," Tetrahedron, vol. 60, No. 48, Nov. 22, 2004, Available Online Oct. 1, 2004, 6 pages.
Lai, C. et al., "Metallo-phosphorylation of alkenes: a highly regioselective reaction of zirconocene-alkene complexes with chlorophosphate," Tetrahedron, vol. 62, No. 26, Jun. 26, 2006, Available Online May 8, 2006, 8 pages.
Perez-Balado, C. et al., "Bispyridinium Dienes: Histone Deacetylase Inhibitors with Selective Activities," Journal of Medicinal Chemistry, vol. 50, No. 10, May 1, 2007, Available Online Apr. 21, 2007, 69 pages.
Minet, I. et al., "Surface-initiated ATRP of PMMA, PS and diblock PS-b-PMMA copolymers from stainless steel modified by 11-(2-bromoisobutyrate)-undecyl-1-phosphonic acid," Journal of Colloid and Interface Science, vol. 332, No. 2, Apr. 15, 2009, Available Online Dec. 31, 2008, 10 pages.
Rele, S. et al., "Low-Valent Titanium Mediated Reductive Cleavage of O/N-Trityl Bonds Via Free Radical Pathway," Synthetic Communications, vol. 32, No. 22, May 22, 2009, 9 pages.
Yang, C. et al., "Hydrophobic-Sheath Segregated Macromolecular Fluorophores: Colloidal Nanoparticles of Polycaprolactone-Grafted Conjugated Polymers with Bright Far-Red/Near-Infrared Emission for Biological Imaging," Biomacromolecules, vol. 17, No. 5, Mar. 24, 2016, 33 pages.

* cited by examiner

ZWITTERIONIC NANOPARTICLES

CROSS-REFERENCE TO RELATED APPLICATIONS

The present application is a U.S. National Phase of International Patent Application Serial No. PCT/EP2018/051288 entitled "ZWITTERIONIC NANOPARTICLES" filed on Jan. 19, 2018. International Patent Application Serial No. PCT/EP2018/051288 claims priority to German Patent Application No. 10 2017 101 057.2 filed on Jan. 20, 2017. The entire contents of each of the above-referenced applications are hereby incorporated by reference for all purposes.

TECHNICAL FIELD

The present invention relates to zwitterionic nanoparticles. In particular, zwitterionic compounds covering the surface of nanoparticles are described. Furthermore, the present invention describes the use of such a preparation and ways and means for producing it.

BACKGROUND AND SUMMARY

Nanoparticles are of great interest because they promise broad technical applications, such as in image display devices, as information storage devices, as biological markers, in diagnostic imaging, as drug transporters, as theranostics, in photovoltaics, as sensors and as catalysts. Due to their small dimensions, nanoparticles can have physicochemical properties that lie between those of molecules and macroscopic materials. For example, nanoparticles made of semiconductor materials may exhibit quantum effects, both of the electron and thus also of the electron gap in all three dimensions, leading to an increase in the band gap of the material with decreasing size of the crystallite. The magnetic properties of the matter also change dramatically depending on the particle size. Similarly, the plasmon absorption of nanoparticles, e.g. gold nanoparticles, depends predominantly on the size and shape of said particles.

The biological effects of nanoparticles, such as the penetration capacity of biological barriers, such as membranes or the skin, or the toxicity of nanoparticles, however, depend not only on the particle properties themselves, but also on changes caused by the introduction of said particles into biological systems. In particular, spontaneous appositions of biological molecules comprising peptide-, protein-, nucleic acid-, or carbohydrate-like structural elements can take place, whereby a "biomolecular corona" may form around the original nanoparticle, which imparts novel, unpredictable and therefore mostly undesirable properties to it and significantly determines the further biological behavior of said particles. This process is known to the person skilled in the art as opsonization, and the resulting undesirable properties are known, inter alia, as "fouling". Said undesired effects represent a major obstacle to the utilization of nanoparticles for biomedical applications, since a high selectivity or specificity of said nanoparticles for the biological target structures, such as cells, tissue, organs, tumors, etc., is indispensable for the targeted manipulation of biological processes.

This is why numerous attempts have been made to suppress these undesired processes by providing said nanoparticles with an appropriate surface finish, thus eliminating the associated disadvantages. In particular, poly(ethylene glycol) (PEG) and oligo(ethylene glycol) (OEG) have been proposed to cover nanoparticle surfaces. Zwitterionic structures were also described for this purpose, with the latter reflecting the state of the art. Thus, WO2013090601 (A2) claims nanoparticles with zwitterionic ligands, in particular to achieve a low degree of non-specific protein absorption. Furthermore, WO2013090601 (A2) claims the functionalization of said nanoparticles with one or more functional groups to give said nanoparticles the desired properties, such as binding to a target molecule or to a receptor.

Thus, the coating of nanoparticles with zwitterionic structures aims at passivating or desensitizing the surface of said nanoparticles against biological influences. This effect is called "stealth" in the Anglo-Saxon literature. The desired effect is that nanoparticles desensitized in this way initially exhibit an indifferent behavior toward biological influences, are thus "invisible" to the respective biological system, and are made suitable for the respective purpose only by linking specific recognition motifs.

US 2014/0235803 A1 relates to nanoparticle-based biotechnological applications with materials that are insensitive to opsonization ("non-fouling materials"), such as poly (ethylene glycol) (PEG) and oligo(ethylene glycol) (OEG).

It is therefore the object of the present invention to further develop zwitterionic nanoparticles of the type mentioned above in an advantageous way, in particular to the effect that an improved and alternative application possibility of nanoparticles is made possible.

SUMMARY OF THE PRESENT INVENTION

This object is achieved according to the invention by a zwitterionic nanoparticle which comprises at least one nanoparticle and a zwitterionic case enclosing the nanoparticle.

Further configurations of the present invention are disclosed herein.

Furthermore, the present invention relates to a composition which comprises at least one zwitterionic nanoparticle in an aqueous solution.

In addition, the present invention in a possible configuration relates to a method of binding a zwitterionic nanoparticle or a composition to a biological molecule or a plurality of biological molecules.

Furthermore, the present invention relates to the use of a zwitterionic nanoparticle and to a composition for a biological event or a biological application.

It was surprisingly found that the procedure described by the state of the art did not result in the expected effects in the present invention, but rather that the nanoparticles in question, which were coated with zwitterionic structures, showed a surprisingly pronounced, structure-dependent selectivity with regard to uptake into cells even without modification with specific recognition motifs.

These effects could also be demonstrated in vivo. For example, said nanoparticles coated with zwitterionic structures showed a surprisingly high selectivity for the uptake in liver sinusoidal endothelial cells (LSECs). It is known from literature that LSECs play a major role in peripheral immune regulation by regulatory T cells.[1] Nanoparticles specifically taken up by LSECs can be loaded with certain autoantigen peptides, for example. By nanoparticle-mediated targeting, LSECs can process and present these autoantigen peptides. Carambia et al. showed that this leads to an induction of regulatory T cells (Tregs) that recognize the autoantigen.[2] Tregs act as immunomodulators. They can attenuate immune responses and thus contribute to tolerance to antigens. In a mouse model of multiple sclerosis (MS), nanoparticles were injected to which peptides of the myelin basic protein were coupled. This resulted in an induction of specific Tregs that could suppress MS progression.[2] This effect depended solely on the induction of the Tregs by the LSECs. Thus, QDQRs-17b might be a way to transport substances specifically into LSECs in order to mediate immunoregulatory effects.

Therefore, QDQRs-17b open up interesting therapeutic perspectives, since they are mainly only absorbed into LSECs but not into Kupffer cells. It is known from literature that LSECs play a major role in peripheral immune regulation by regulatory T cells.[1] Nanoparticles that are specifically taken up by LSECs can, for example, be coupled with certain autoantigen peptides. By nanoparticle-mediated targeting, LSECs can process and present these autoantigen peptides. Carambia et al. showed that this leads to an induction of regulatory T cells (Tregs) that recognize the autoantigen.[2] Tregs act as immunomodulators. They can attenuate immune responses and thus contribute to tolerance to antigens. In a mouse model of multiple sclerosis (MS), nanoparticles were injected to which peptides of the myelin basic protein were coupled. This resulted in an induction of specific Tregs that could suppress MS progression.[2] This effect depended solely on the induction of the Tregs by the LSECs. Thus, QDQRs-17b might be a way to transport substances specifically into LSECs in order to mediate immunoregulatory effects.

In other words:

In particular, it may be envisaged that the biological application is or includes an immunological application. The term "immunological application" is to be understood as comprising one or more applications involving the physical defence against pathogens such as bacteria, viruses and fungi as well as other exogenous substances such as biological toxins and environmental toxins and also disturbances and malfunctions of these defence mechanisms. Immunological applications can be found, for example, in the field of immunochemistry, immunogenetics, immunopathology or clinical immunology.

The immunological application may be or include a modulation of inflammation, in particular where the modulation of inflammation is or includes reduction of auto-aggressive inflammation.

Furthermore, the immunological application may be or include a modulation of an autoimmune disease.

An application in connection with the treatment of multiple sclerosis (MS) or other autoimmune diseases such as lupus erythematosus, type 1 diabetes or the like is conceivable.

It is also conceivable that the immunological application is or includes a modulation of an allergy.

The immunological application may be or include a suppression of immunological responses against biologicals. The term "biologicals" is also referred to as a biopharmaceutical. Biopharmaceuticals or biologicals are drugs that are produced using biotechnology and genetically modified organisms. Against biologicals, which are used for the treatment of many serious diseases such as tumors and others, immune responses can be triggered which make the treatment of patients difficult or impossible.

The biological application may be or comprise a modulation of a differentiation of a cell, especially a liver cell, for example a hepatic endothelial cell. It is conceivable, for example, to halt the trans-differentiation or de-differentiation of a cell, e.g. a liver cell, or to return a transdifferentiated cell to the state prior to trans-differentiation or dedifferentiation or to initiate this process accordingly. It is conceivable that it could be used in connection with the treatment of liver diseases such as liver fibrosis, liver cirrhosis, liver tumors or the like.

Thus, the present invention is excellently suited to specifically control the uptake of said nanoparticles into cells by structural variations of the zwitterionic motifs on the surface of nanoparticles. Such an application has not yet been described so far and is therefore new.

BRIEF DESCRIPTION OF THE FIGURES

In the Figures:

FIG. 2 shows microscopic images of A549 cells after 16 hours incubation with different concentrations of QDQRs-17a;

DETAILED DESCRIPTION OF THE TERMS USED IN THE PRESENT INVENTION

Figure 1:
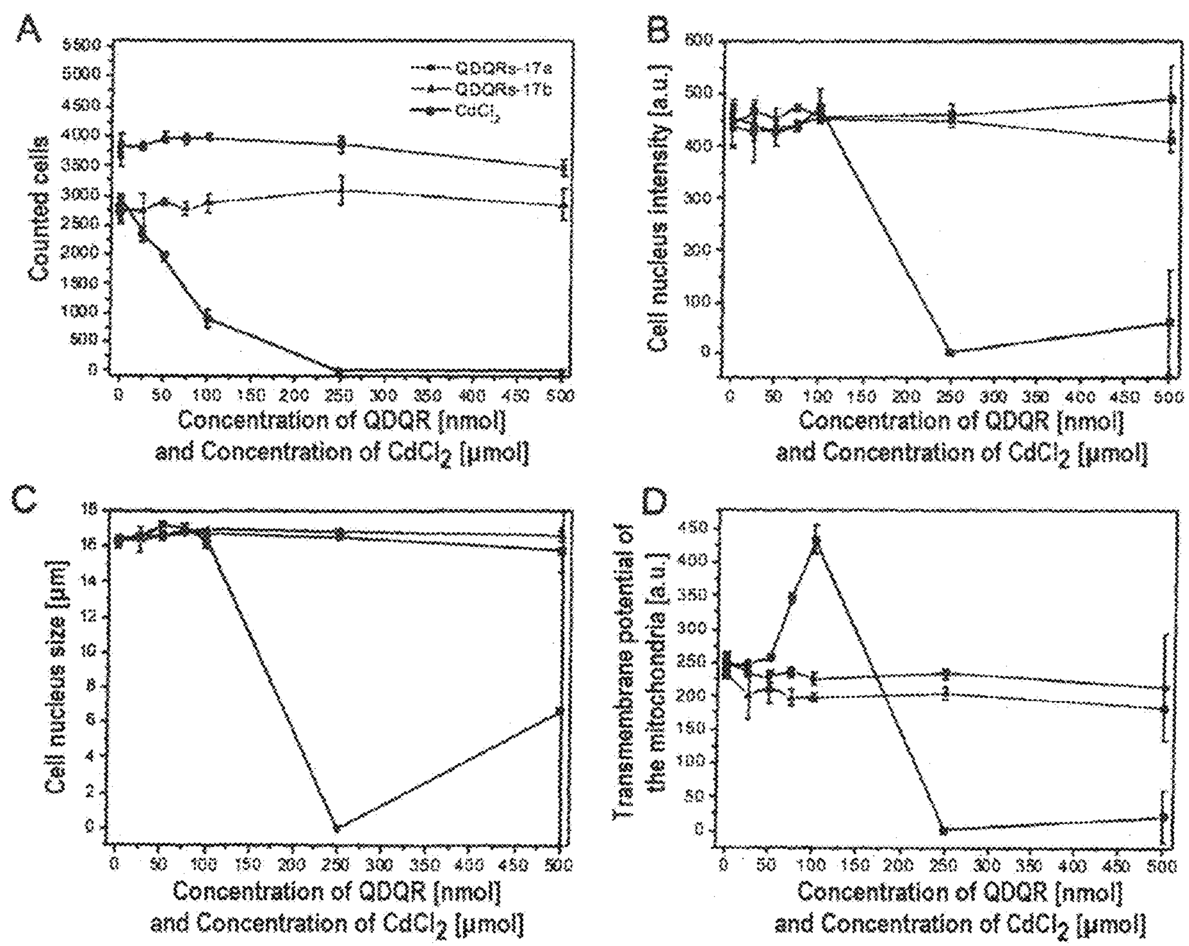
FIG. 1 shows a quantification of the toxicity tests of QDQRs-17a and QDQRs-17b and cadmium chloride.

The present invention describes nanoparticles with an organic zwitterionic case, said nanoparticles being suitable for the transport of molecules, in particular drug molecules, and optionally having superparamagnetic, plasmonic or fluorescent properties, including combinations of said properties. Nanoparticles in the sense of the invention are spatial objects which have an extension of 1 to 1000 nm in at least one spatial direction. The nanoparticles in question may be available in the form of both solid particles and hollow bodies in various shapes which include spherical, elongated, e.g. rod-shaped, elliptical, egg-shaped, dumbbell-shaped, ring-shaped, cube-shaped or cube-like, prismatic or cylindrical, regularly or irregularly multiply facetted geometric bodies, polygonal plates with e.g. a triangular, square or hexagonal shape, flakes, multi-arm or star-shaped bodies such as tetrapods, or a wire-like shape, etc. Said nanoparticles may optionally be coated with at least one shell made of a material other than that of the core. The term "nanoparticles" includes the terms "nanocrystal" or "ultra-small particle".

The detailed description of the invention should be preceded by the statement that this invention is not limited to the methods, devices or preparations, as these can of course be modified. Furthermore, the terms used to describe the invention are merely intended to explain certain embodiments and in no way to restrict the scope of the invention. Thus, the specific or indefinite singular article "a" and "the" also includes the plural, unless the context clearly requires the opposite. Consequently, for example, the term "a cell" includes a large number of cells, "a nanoparticle" a large number of nanoparticles, "a biomolecule" such as DNA, protein, peptide, carbohydrate, etc. includes a large number of biomolecules, and so on.

All technical and scientific terms have the meaning as understood by the person skilled in the field of the present invention, unless otherwise defined or the context suggests a different meaning. Although any other method or other substances, similar to or equivalent to those described here, are also suitable for practicing or testing the invention, the preferred methods and substances are described below.

All publications mentioned here are hereby included by reference for the purpose of disclosure and description of the individual materials and processes for which the relevant reference has been cited. These publications, as described here, are provided only for disclosure thereof prior to the filing date of the present invention. However, it cannot be inferred from this what can be interpreted as an admission to the effect that the invention is not entitled to pre-date such disclosure as prior art. In describing the present invention, the following terms are used and shall be understood as defined below.

The term "inorganic nanocrystal" means a particle, generally a semiconductor particle, or a nanocrystalline particle which is not based on semiconductor materials, in particular a rare earth-doped metal oxide particle, or a rare earth-doped salt-like particle, or an oxidic or metallic particle with a diameter in the range of 1 nm to 1000 nm, preferably in the range of approx. 2 nm to 100 nm. The terms "semiconductor nanocrystal" and "quantum dot", "quantum rod", "quantum dot rod" or the abbreviations QD, QDs, QR, QRs, QDR, QDRs, SCNC or SCNCs are used interchangeably to denote semiconductor nanoparticles consisting of an inorganic substance which is optionally luminescent (i.e. capable of emitting electromagnetic radiation upon excitation) and comprises an inner core of one or more first semiconductor materials optionally enclosed by a sheath or "shell" of a second semiconductor material. For example, the encasing shell material may have a bandgap energy higher than that of the core material and selected such that the inter-atomic distances are similar to those of the core material. A semiconductor nanocrystal encased in a semiconductor shell is referred to as a "core/shell semiconductor nano crystal".

Semiconductors are described in particular by their electrical conductivity, which lies between that of a conductor and that of a non-conductor. Suitable semiconductor materials may be the following materials, without being limited to them, and consist of a first element selected from groups 2 and 12 of the Periodic Table of the Elements and a second element selected from group 16 of the Periodic Table (e.g. ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like); further, materials consisting of a first element selected from Group 15 of the Periodic Table of the Elements and a second element from Group 15 (e.g. GaN, GaP, GaAs, GaSb, InN, InP, InAs, InSb, etc.); furthermore, materials consisting of Group 14 of the Periodic Table of the Elements (Ge, Si, etc.); materials such as PbS, PbSe, PbTe, etc., materials such as CuInS, CuInGaS, etc., and alloys and mixtures thereof. As used here, all information on the Periodic Table of the Elements and its groups refers to the new IUPAC element group numbering system as described in Handbook of Chemistry and Physics, 61 st 20 Edition (CRC Press, 2000).

An SCNC (semi conductor nano crystal) is optionally surrounded by a layer made of an organic material. This organic layer may consist of a variety of substances and is distinguished by its affinity to the surface of the SCNC. In general, the coating material may consist of small organic individual molecules, polymers (or monomers that can be used in a polymerization reaction), inorganic complexes, or an extended crystalline structure. This coating can serve to impart the solubility of such a coated SCNC in a chosen solvent, certain functionalities or binding properties. In addition, the coating can also be used to adjust the optical properties of the SCNC. Accordingly, the terms "semiconductor nano crystal", "SCNC", "quantum dot", as described here, also include organically encapsulated SCNC cores as well as organically encapsulated core/shell SCNCs.

"Monodisperse particles" include a stock of particles in which at least 60%, but preferably between 75% and 90%, of the particles in the stock correspond to a given size range. A stock of monodisperse particles has a particle diameter deviation of less than 10%, but preferably a deviation of less than 5% from the root mean square (RMS) of the stock. The term "one or more sizes of SCNC" is used to mean "one or more particle size distributions". The expert will understand that certain sizes of nanoparticles are actually obtained as particle size distributions.

"Luminescence" is to be understood as a process in which an object emits electromagnetic radiation (light). Luminescence occurs when a system changes from an excited state to a lower-energy state, with the energy delivered being released in the form of photons. These energy states may have various forms, such as oscillation energy, rotational energy, may be of electronic nature, or exist in any combination of these energies. The transition that causes luminescence can be triggered by chemical energy stored in the system or by an external source. The external energy source can be supplied in various forms, including chemical, thermal, electrical, magnetic, electromagnetic, physical, or any other form capable of causing excitation to a higher energy state than the ground state. For example, a system can be excited by the absorption of at least one photon, by introduction into an electric field, or by a chemical redox reaction. The energy of the photon emitted during luminescence can be in the range from low-energy microwave radiation to high-energy X-ray radiation. Typically, luminescence refers to photons in the range from UV to IR radiation.

"Biological molecule" or "biomolecule" refers to any type of molecule found in biological applications, see following non-limiting enumeration: Optionally glycosylated proteins, e.g. antibodies, nano bodies, parts of antibodies such as single chain antibodies, Fab fragments, viral proteins, lectins, peptides including polyamino acids, nucleic acids including deoxyribonucleic acids (DNA), ribonucleic acids (RNA, siRNA, miRNA), "locked nucleic acid" (LNA), aptamers, lipids. Steroids, messengers, prions, carbohydrates, small molecules, etc.

The term "micelle" generally refers to a colloidal arrangement of surfactants distributed in a liquid, and the term "surfactant" refers to a surface active agent that reduces the surface tension of a liquid, usually organic compounds that are amphiphilic. The term "transfection" means the intentional or unintentional introduction of material, such as micelle-encapsulated nanoparticles into cells. The term "marking" generally refers to the intentional or unintentional attachment of material, such as micelle-encapsulated nanoparticles, to a cell, a biological molecule or a biological sample. Such material may, for example, be attached to or within the cell. Transfection and marking of a cell or the marking of a biological molecule or a biological sample are examples of biological applications. The term "biological event" includes an interaction of biological structures, a biological process, structural changes in a biological compound or a change in a biological process. The term "biological sample" means a tissue sample or a fluid derived from an individual, including but not limited to e.g. plasma, serum, spinal fluid, sperm, lymphatic fluid, external sections of the skin, respiratory system, digestive system, urogenital tract, tear fluid, saliva, milk, blood cells, tumors, organs, and samples from in vitro cell culture components (including but not limited to processed cell culture medium derived from cell growth in cell cultures, optionally from virally infected cells, recombinant cells and cell components). Terms such as "bio-functionalized", "bonded", "attached", "linked" or "conjugated" are used interchangeably here and include both direct and indirect linking, attachment or conjugation, unless the context requires otherwise.

In this context, the term "zwitterionic nanoparticle" means a spatial object having an extension of 1 to 1000 nm in at least one spatial direction, said extension being enclosed by a zwitterionic case. In various embodiments, this case may consist of individual molecules that are not covalently connected to each other. The outer shape of the case can be produced in different embodiments of the invention by ionic, non-ionic, electrostatic or covalent interactions, based on thermodynamic, such as negentropic effects, such as micelle formation, or by combinations of these binding forces. Alternatively, the formation of this case may be produced by association of the case components on at least one formative inorganic nanocrystal, such as a nanocrystal consisting of semiconductors, silicates, salts, metals or metal oxides, or on a nanoparticle consisting of organic components, such as polymers or solid lipids, or by intermolecular interactions without the involvement of a formative nanoparticle. Thus, the present invention also provides a preparation consisting of at least one micelle in a non-aqueous solution. Said micelle may encapsulate one or more nanoparticles, which may be monodisperse nanoparticles. Said micelle may optionally contain at least one active ingredient instead of one or more nanoparticles. Said micelle may optionally be empty.

The term "zwitterionic compound" includes the terms "zwitterionic ligand" or "zwitterionic group". The terms "zwitterion" and "betaine" are also interchangeable.

Said zwitterionic compounds have the general formula (I):

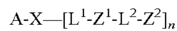

$$A\text{-}X\text{—}[L^1\text{-}Z^1\text{-}L^2\text{-}Z^2]_n \quad \text{Formula (I)}$$

In this formula, A is optionally a group having affinity for the surface of the inorganic nanoparticle, or is an at least divalent atom, preferably from the group C, N, O, S, P or Si, capable of forming a covalent bond to the nanoparticle. X is an optional branching element such that X has, in addition to the bond to A, at least one further bond to $L_1$. X optionally represents a bond or an at least divalent atom, preferably from the group C, N, O, S, P or Si. $L^1$ and $L^2$ are mutually independent linker groups; $Z^1$ includes a first charged or ionizable group; $Z^2$ includes a second charged or ionizable group, provided that they are opposite in case $Z^1$ or $Z^2$ carry charges. n comprises the integers between 1 and the maximum valence of X−1.

A includes or optionally comprises at least one amino, mercapto, dithiocarbamate, carboxylate, phosphate, phosphonate group.

$L^1$ and $L^2$ are mutually independent, linear or branched, optionally saturated or unsaturated hydrocarbon chains having one to forty carbon atoms, which may optionally contain heteroatoms selected from the group consisting of N, O, P, Si and S.

The following examples are intended to illustrate the invention without limiting its scope.

Example 1

Preparation of tert-butyl(3-(dimethylamino)propyl)(methyl)carbamate

N,N,N'-trimethylpropane-1,3-diamine (586 μL, 3.98 mmol) and triethylamine (TEA) (1.6 mL, 11.54 mmol) were dissolved in dry dichloromethane (DCM) (12 mL) and cooled in an ice bath. Subsequently, Di-tert-butyl dicarbonate (1 mL, 4.35 mmol) was dissolved in dry DCM (2 mL) and slowly added drop-wise at a temperature below 2° C. The reaction mixture was stirred for a further 45 minutes at 0° C. and overnight (15 hours) at room temperature. For reprocessing, the organic phase was extracted with saturated NaCl, saturated $NaHCO_3$ solution and $H_2O$ (5 mL each), dried over $Na_2SO_4$ and the solvent was removed in vacuum. The product had the form of a light yellow oil.

Yield: 87%

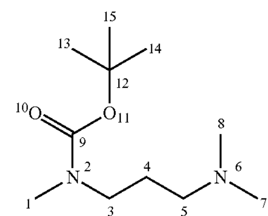

$^1$H-NMR (600 MHz, $CDCl_3$): δ [ppm]=7.26 ($CDCl_3$); 3.28-3.20 (m, 2H, H-3); 2.84 (s, 3H, H-1); 2.31-2.25 (m, 2H, H-5); 2.23 (s, 6H, H-7 and H-8); 1.73-1.66 (m, 2H, H-4) and 1.45 (s, 9H, H-13, H-14 and H-15).

Example 2

Preparation of 3-((3-((tert-butoxycarbonyl)(methyl)amino)propyl)-di-methylammonio)-propane-1-sulfonate Tert-butyl(3-(dimethylamino)propyl)(methyl)carbamate (1.11 g, 5.13 mmol) and 1,3-propane sultone (677 μL, 7.70 mmol) were dissolved in dry DCM (25 mL). The reaction mixture was stirred for five days at room temperature to form a pearly solid. The solvent was largely removed at a rotary evaporator and the excess of 1,3-propane sultone separated by repeated washing with dry THF. The residue was dried in vacuum and the product was present as a colorless solid.

Yield: 81%

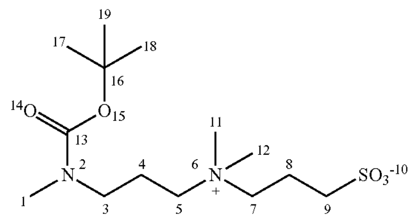

$^1$H-NMR (400 MHz, $D_2O$): δ [ppm]=4.79 ($D_2O$); 3.55-3.51 (m, 2H, H-7); 3.42-3.35 (m, 4H, H-3 and H-5); 3.16 (s, 6H, H-11 and H-12); 3.02 (t, 2H, J=7.2 Hz, H-9), 2.91 (s, 3H, H-1); 2.29-2.21 (m, 2H, H-8), 2.12-2.04 (m, 2H, H-4) and 1.50 (s, 9H, H-17, H-18 and H-19).

$^{13}$C-NMR (100 MHz, $D_2O$): δ [ppm]=157.6 (C-13); 81.8 (C-16); 62.3 (C-5); 62.0 (C-7); 50.6 (C-11 and C-12); 47.2 (C-9); 45.0 (C-3); 33.8 (C-1); 27.7 (C-17, C-18 and C-19); 20.8 (C-4) and 18.2 (C-8).

ESI-MS: (m/z) calc. for $C_{14}H_{31}N_2O_5S$ $(M+H)^+$ 339.1948, ascertained 339.1955.

IR (neat): υ [$cm^{-1}$]=2973; 2925; 1679 (C═O); 1199 (S═O); 1161 (C—O); 1034 (S═O), 605 and 524.

Example 3

Preparation of 3-(dimethyl(3-(methylamino)propyl)ammonio)propane-1-sulfonate 3-((3-((tert-butoxycarbonyl)(methyl)amino)propyl)dimethylammonio)-propane-1-sulfonate (435 mg, 1.29 mmol) was dissolved in ultrapure water (13 mL) and the reaction vessel was rinsed with nitrogen. The solution was then heated to 135° C. in the microwave for 90 minutes. After removing the water, the crude product was dissolved in MeOH (8 mL), mixed with Amberlyst A26 and stirred for four hours at room temperature. The Amberlyst was then filtered off and the solvent removed in the rotary evaporator. For complete drying, the residue was absorbed in a small amount of ultrapure water and lyophilized. The product was present as a colorless, strongly hygroscopic solid.

Yield: 88%

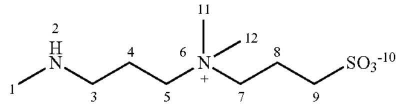

$^1$H-NMR (400 MHz, $D_2O$): δ [ppm]=4.79 ($D_2O$); 3.52-3.48 (m, 2H, H-7); 3.41-3.37 (m, 2H, H-5); 3.13 (s, 6H, H-11 and H-12); 3.00 (t, 2H, J=7.1 Hz, H-9); 2.76-2.72 (m, 2H, H-3); 2.42 (s, 3H, H-1); 2.27-2.19 (m, 2H, H-8) and 2.06-1.99 (m, 2H, H-4).

$^{13}$C-NMR (100 MHz, $D_2O$): δ [ppm]=62.2 (C-7); 61.9 (C-5); 50.7 (C-11 and C-12); 47.1 (C-9); 46.6 (C-3); 34.1 (C-1); 21.2 (C-4) and 18.1 (C-8).

ESI-MS: (m/z) calc. for $C_9H_{23}N_2O_3S$ $(M+H)^+$ 239.1424, ascertained 239.1430.

IR (neat): υ [$cm^{-1}$]=3432; 3034; 2968; 1164 (S═O); 1032 (S═O), 601 and 521.

Example 4

Preparation of tert-butyl-bis(3-(dimethylamino)propyl)carbamate 3,3'-Iminobis-N,N-dimethylpropylamine (891 μL, 4.00 mmol) and TEA (1.6 mL, 11.54 mmol) were dissolved in dry DCM (12 mL) and cooled in an ice bath. Di-tert-butyldicarbonate (1 mL, 4.35 mmol) was then dissolved in dry DCM (2 mL) and slowly added in drops at a temperature below 3° C. The reaction mixture was stirred for further 90 minutes at 1° C. and overnight (15 hours) at room temperature. For reprocessing, the organic phase was extracted with saturated NaCl, saturated $NaHCO_3$ solution and $H_2O$ (5 mL each), dried over $Na_2SO_4$ and the solvent was removed in vacuum. The product had the form of a light yellow oil.

Yield: 68%

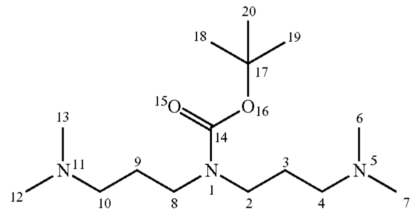

$^1$H-NMR (400 MHz, $CDCl_3$): δ [ppm]=7.26 ppm ($CDCl_3$); 3.24-3.17 (m, 4H, H-2 and H-8); 2.25 (t, 4H, J=7.4 Hz, H-4 and H-10); 2.21 (s, 12H, H-6, H-7, H-12 and H-13); 1.72-1.65 (m, 4H, H-3 and H-9) and 1.45 (s, 9H, H-18, H-19 and H-20).

Example 5

Preparation of 3,3'-(((((tert-butoxycarbonyl)azadiyl)bis(propane-3,1-diyl))bis(dimethylammoniodiyl))bis(propane-1-sulfonate)

Tert-butyl-bis(3-(dimethylamino)propyl)carbamate (500 mg, 1.74 mmol) and 1,3-propane sultone (459 μL, 5.22 mmol) were dissolved in dry DCM (20 mL). After 24 hours, a colorless solid had formed and the resulting suspension had such a high viscosity that dry DCM (20 mL) was added again. The reaction mixture was stirred at room temperature for a further three days. The solvent was removed as far as possible at the rotary evaporator and the excess of 1,3-propane sultone was separated by repeated washing with dry THF. The residue was dried in vacuum and the product was present as a colorless solid.

Yield: 91%

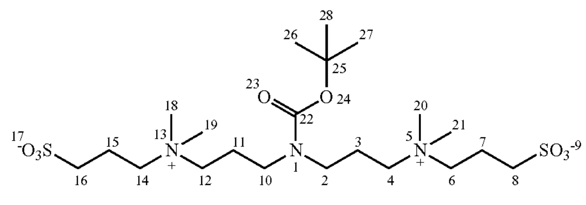

$^1$H-NMR (400 MHz, $D_2O$): δ [ppm]=4.79 ($D_2O$); 3.55-3.51 (m, 4H, H-6 and H-14); 3.40-3.36 (m, 8H, H-2, H-4, H-10 and H-12); 3.16 (s, 12H, H-18, H-19, H-20 and H-21); 3.02 (t, 4H, J=7.1 Hz, H-8 and H-16); 2.27-2.21 (m, 4H, H-7 and H-15); 2.13-2.05 (m, 4H, H-3 and H-11) and 1.52 (s, 9H, H-26, H-27 and H-28).

$^{13}$C-NMR (100 MHz, $D_2O$): δ [ppm]=157.1 (C-22); 82.3 (C-25); 62.2 (C-4, C-6, C-12 and C-14); 50.8 (C-18, C-19, C-20 and C-21); 47.2 (C-8 and C-16); 40.3 (C-2 and C-10); 27.7 (C-26, C-27 and C-28); 22.7 (C-3 and C-11) and 18.2 (C-7 and C-15).

ESI-MS: (m/z) calc. for $C_{21}H_{46}N_3O_8S_2$ $(M+H)^+$ 532.2721, ascertained 532.2741.

IR (neat): υ [$cm^{-1}$]=3452; 3038; 2974; 1676 (C═O), 1157 (C—O); 1033 (S═O), 602 and 521.

Example 6

Preparation of the 3,3'-((Azadiylbis(propane-3,1-diyl))bis(dimethylammoniodiyl))bis-(propane-1-sulfonate)

3,3'-(((((tert-butoxycarbonyl)azanediyl)bis(propane-3,1-diyl))bis(dimethylammoniodiyl))bis-(propane-1-sulfonate) (783 mg, 1.47 mmol) was dissolved in ultrapure water (14.7 mL). The reaction vessel was rinsed with nitrogen and the solution was heated to 135° C. for 90 minutes in the microwave. After lyophilization, the product was dissolved in MeOH (10 mL) and stirred overnight in the presence of Amberlyst A 26. After filtering off the Amberlyst, the solvent was removed at the rotary evaporator and the residue lyophilized again after adding a small amount of ultrapure water. The product had the form of a light yellow, foam-like solid.

Yield: 71%

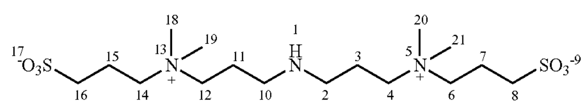

$^1$H-NMR (400 MHz, $D_2O$): δ [ppm]=4.79 ($D_2O$); 3.55-3.51 (m, 4H, H-4 and H-12); 3.44-3.39 (4H, m, H-6 and H-14); 3.16 (s, 12H, H-18, H-19, H-20 and H-21); 3.03 (t, 4H, J=7.1 Hz, H-8 and H-16); 2.77-2.74 (m, 4H, H-2 and H-10); 2.30-2.22 (m, 4H, H-7 and H-15) and 2.07-1.99 (m, 4H, H-3 and H-11).

$^{13}$C-NMR (100 MHz, $D_2O$): δ [ppm]=62.2 (C-4 and C-12); 62.00 (C-6 and C-14); 50.7 (C-18, C-19, C-20 and C-21); 47.2 (C-8 and C-16); 44.9 (C-2 and C-10); 21.7 (C-7 and C-15) and 18.1 (C-3 and C-11).

ESI-MS: (m/z) calc. for $C_{16}H_{38}N_3O_6S_2(M+H)^+$ 432.2197, ascertained 432.2216.

IR (neat): υ [$cm^{-1}$]=3434; 3038; 2968; 2824; 1167 (S═O); 1033 (S═O), 602 and 521.

Example 7

Preparation of 1-((3-((tert-butoxycarbonyl)(methyl)amino)dimethyl-ammonio)hex-5-en-3-sulfonate Tert-butyl(3-(dimethylamino)propyl)(methyl)carbamate (434 mg, 2.01 mmol) and 3-allyl-1,2-oxathiolane-2,2-dioxide (442 mg, 2.72 mmol) were dissolved in dry DCM (20 mL). The reaction mixture was stirred for five days at room temperature and a pearly solid was formed. The solvent was largely removed at the rotary evaporator and the excess of 3-Allyl-1,2-oxathiolane-2,2-dioxide was separated by repeated washing with dry THF. The residue was dried in vacuum and the product was present as a colorless solid.

Yield: 83%

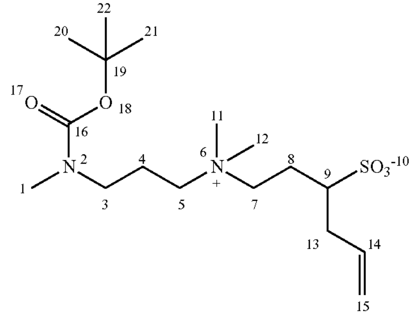

$^1$H-NMR (400 MHz, $D_2O$): δ [ppm]=5.98-5.87 (m, 1H, H-14); 5.31-5.22 (m, 2H, H-15); 4.79 ($D_2O$); 3.67-3.60 (m, 1H, H-7a); 3.55-3.31 (m, 5H, H-3, H-5 and H-7b); 3.14 (s, 6H, H-11 and H-12); 3.04-2.98 (m, 1H, H-9), 2.91 (s, 3H, H-1); 2.79-2.72 (m, 1H, H-13a); 2.42-2.36 (m, 1H, H-13b); 2.26-2.14 (m, 2H, H-8), 2.08-2.03 (m, 2H, H-4) and 1.50 (s, 9H, H-20, H-21 and H-22).

$^{13}$C-NMR (100 MHz, $D_2O$): δ [ppm]=157.1 (C-16); 134.2 (C-14); 118.4 (C-15); 81.8 (C-19); 61.6 (C-5 and C-7); 56.5 (C-9); 50.8 (C-11 and C-12); 45.3 (C-3); 34.0 (C-13); 33.7 (C-1); 27.7 (C-20, C-21 and C-22); 22.2 (C-8) and 20.8 (C-4).

ESI-MS: (m/z) calc. for $C_{17}H_{35}N_2O_5S$ $(M+H)^+$ 379.2261, ascertained 379.2284.

IR (neat): υ [$cm^{-1}$]=2976; 1679 (C═O); 1199 (S═O); 1172 (C—O); 1028 (S═O), 602 and 537.

Example 8

Preparation of 1-(dimethyl(3-methylamino)propyl) ammonio)hex-5-ene-3-sulfonate 1-((3-((tert-butoxycarbonyl)(methyl)amino)dimethylammonio)hex-5-en-3-sulfonate (568 mg, 1.50 mmol) was dissolved in ultrapure water (15 mL). The reaction vessel was rinsed with nitrogen and the solution was heated to 135° C. in the microwave for 90 minutes. After lyophilization, the product was dissolved in MeOH (10 mL) and stirred overnight in the presence of Amberlyst A 26. After filtering off the Amberlyst, the solvent was removed at the rotary evaporator and the residue lyophilized again after adding a small amount of ultrapure water. The product had the form of a light yellow, foam-like solid.

Yield: 90%.

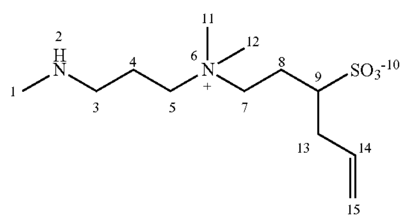

$^1$H-NMR (400 MHz, $D_2O$): δ [ppm]=5.97-5.87 (m, 1H, H-14); 5.31-5.23 (m, 2H, H-15); 4.79 ($D_2O$); 3.68-3.60 (m, 1H, H-7a); 3.54-3.47 (m, 1H, H-7b); 3.41-3.37 (m, 2H, H-5); 3.13 (s, 6H, H-11 and H-12); 3.04-2.98 (m, 1H, H-9);

2.79-2.72 (m, 3H, H-3 and H-13a); 2.43 (s, 3H, H-1); 2.42-2.36 (m, 1H, H-13b); 2.27-2.11 (m, 2H, H-8) and 2.06-1.98 (m, 2H, H-4).

$^{13}$C-NMR (100 MHz, $D_2O$): δ [ppm]=134.2 (C-14); 118.4 (C-15); 61.7 (C-5); 61.5 (C-7); 56.5 (C-9); 50.7 (C-11 and C-12); 46.7 (C-3); 34.2 (C-1); 34.0 (C-13); 22.2 (C-8) and 21.3 (C-4).

ESI-MS: (m/z) calc. for $C_{12}H_{27}N_2O_3S$ $(M+H)^+$ 279.1737, ascertained 279.1751.

IR (neat): υ [cm$^{-1}$]=3453; 3028; 2942; 2847; 2793; 1173 (S═O); 1028 (S═O), 601 and 532.

Example 9

Preparation of 11-bromo-N-methylundecanamide 11-bromoundecanoic acid (5.00 g, 18.85 mmol) was dissolved in dry DCM (100 mL) and a solution of oxalyl chloride (1.7 mL, 19.82 mmol) was added in drops to dry DCM (10 mL) within five minutes. An evolution of gas was observed at the beginning and the reaction mixture was stirred for one hour at room temperature. Subsequently, the solvent and excess oxalyl chloride were removed in vacuum and the raw product dissolved in dry $Et_2O$ (12 mL). The activated acid was added in drops to an aqueous methylamine solution (40%, 4.3 mL, 49.80 mmol) cooled in an ice bath, and a colorless precipitate was immediately formed. The precipitate was filtered off and washed with $H_2O$ (50 mL). After drying in vacuum, the product was present as a colorless solid.

Yield: 89%

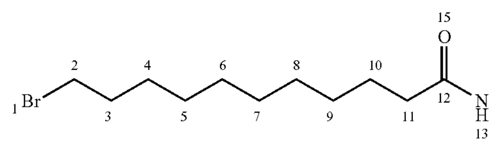

$^1$H-NMR (400 MHz, $CDCl_3$): δ [ppm]=7.26 ($CDCl_3$); 5.82 (brs, 1H, NH); 3.40 (t, 2H, J=6.9 Hz, H-2); 2.82 (s, 3H, H-14); 2.21 (t, 2H, J=7.6 Hz, H-11); 1.88-1.81 (m, 2H, H-3); 1.65-1.60 (m, 2H, H-10); 1.43-1.38 (m, 2H, H-4) and 1.34-1.25 (m, 10H, H-5 to H-9).

Example 10

Preparation of 11-(dimethylamino)-N-methylundecanamide 11-bromo-N-methylundecanamide (1.39 g, 5.00 mmol) and a solution of dimethylamine in EtOH (33% by weight, 9 mL, 50.40 mmol) were heated to 60° C. in the microwave for two hours. The solvent and the excess dimethylamine were removed in vacuum and the hydrobromide of the product was obtained in the form of a light yellow solid. The solid was suspended in MTBE (10 mL) and extracted with 1 M NaOH (5 mL). The organic phase was dried over $Na_2SO_4$ and the solvent was removed in vacuum. The product had the form of a light yellow solid.

Yield: 91%

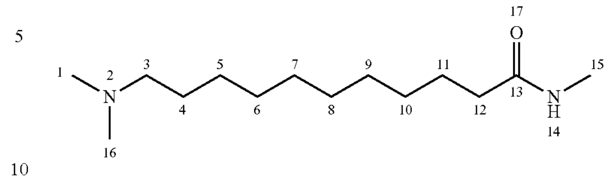

$^1$H-NMR (400 MHz, $CDCl_3$): δ [ppm]=7.26 ($CDCl_3$); 5.50 (brs, 1H, NH); 2.80 (s, 3H, H-15); 2.33 (t, 2H, J=7.7 Hz, H-3); 2.29 (s, 6H, H-1 and H-16); 2.15 (t, 2H, J=7.6 Hz, H-12); 1.65-1.57 (m, 2H, H-11); 1.53-1.46 (m, 2H, H-4) and 1.34-1.22 (m, 12H, H-5 to H-10).

Example 11

Preparation of N,N,N'-Trimethylundecane-1,11-diamine $LiAlH_4$ (2 M in dry THF, 2.7 mL, 5.40 mmol) in dry THF (5 mL) was cooled to −2° C. in an ice bath. At this temperature, a solution of 11-(dimethylamino)-N-methylundecanamide (660 mg, 2.72 mmol) in dry THF (15 mL) was slowly added in drops. The solution became turbid during addition. After addition, the reaction mixture was slowly heated to room temperature and then heated under reflux for three hours. The reaction mixture was then cooled to 0° C. and carefully quenched with $H_2O$ (205 μL), 15% NaOH (205 μL) and again $H_2O$ (615 μL), whereby the inorganic salts precipitated. The suspension was stirred at room temperature for a further 30 minutes. To separate the solid, the suspension was centrifuged and the solid washed several times with dry THF. The combined organic phases were dried over $Na_2SO_4$ and the solvent was removed in vacuum. The raw product had the form of a yellow oil and was used without further reprocessing.

Yield: 96% (raw yield)

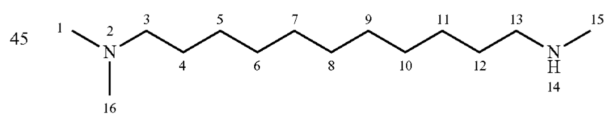

$^1$H-NMR (600 MHz, $CDCl_3$): δ [ppm]=7.26 ($CDCl_3$); 2.55 (t, 2H, J=7.2 Hz, H-13); 2.43 (s, 3H, H-15); 2.23 (t, 2H, J=7.4 Hz, H-3); 2.21 (s, 6H, H-1 and H-16); 1.51-1.43 (m, 4H, H-4 and H-12) and 1.34-1.23 (m, 14H, H-5 to H-11).

Example 12

Preparation of the tert-butyl(11-(dimethylamino) undecyl(methyl)carbamate

Di-tert-butyl dicarbonate (512 μL, 2.23 mmol) and Amberlyst 15 (76 mg, 15 wt. %) were put in a round flask. Subsequently, N,N,N'-trimethylundecane-1,11-diamine (505 mg, 2.21 mmol) was added in drops and a strong evolution of gas was observed. The reaction mixture was stirred for 15 minutes, then diluted with DCM (22 mL), and the Amberlyst was filtered off. The solvent was removed at the rotary evaporator and the raw product was purified by column chromatography (DCM/methanol/TEA). The product had the form of a light yellow oil.

Yield: 57%

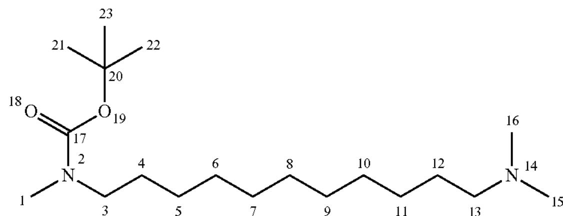

$^1$H-NMR (400 MHz, $CDCl_3$): δ [ppm]=7.26 ($CDCl_3$); 3.17 (t, 2H, J=6.9 Hz, H-3); 2.82 (s, 3H, H-1); 2.27 (t, 2H, J=7.6 Hz, H-13); 2.24 (s, 6H, H-15 and H-16); 1.52-1.46 (m, 4H, H-4 and H-12); 1.45 (s, 9H, H-21, H-22 and H-23) and 1.28-1.26 (m, 14H, H-5 to H-11).

$^{13}$C-NMR (100 MHz, $CDCl_3$): δ [ppm]=156.0 (C-17); 79.2 (C-20); 77.2 ($CDCl_3$); 60.0 (C-13); 48.7 (C-3); 45.5 (C-15 and C-16); 34.2 (C-1); 29.7-29.5 (C-5 to C-11); 28.6 (C-21, C-22 and C-23); 27.8-27.6 (C-4 and C-12) and 26.9 (C-5 to C-11).

ESI-MS: (m/z) calc. for $C_{19}H_{41}N_2O_2$ $(M+H)^+$ 329.3163, ascertained 329.3169.

IR (neat): υ [$cm^{-1}$]=2973; 2925; 2854; 1696 (C═O) and 1153 (C—O).

Example 13

Preparation of 3-((11-((tert-butoxycarbonyl)(methyl) amino)undecyl)-dimethylammonio)-propane-1-sulfonate Tert-butyl-(11-(dimethylamino)undecyl(methyl)carbamate (250 mg, 0.76 mmol) and 1,3-propane sultone (105 μL, 1.17 mmol) were dissolved in dry DCM (10 mL). The reaction mixture was stirred at room temperature for 11 days. The solvent was largely removed at the rotary evaporator and the excess 1,3-propane sultone was separated by repeated washing with dry THF. The residue was dried in vacuum and the product was present as a colorless solid.

Yield: 77%

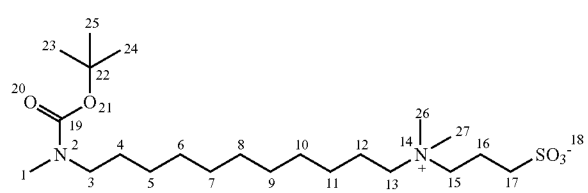

$^1$H-NMR (600 MHz, $D_2O$): δ [ppm]=4.79 ($D_2O$); 3.50-3.47 (m, 2H, H-15); 3.35-3.32 (m, 2H, H-13); 3.24-3.25 (m, 2H, H-3); 3.12 (s, 6H, H-26 and H-27); 2.99 (t, 2H, J=7.1 Hz, H-17); 2.84 (s, 3H, H-1); 2.26-2.20 (m, 2H, H-16); 1.79-1.77 (m, 2H, H-12); 1.57-1.53 (m, 2H, H-4); 1.46 (s, 9H, H-23, H-24 and H-25); 1.38 (m, 4H, H-10 and H-11); 1.33 (m, 8H, H-6 to H-9) and 1.30-1.28 (m, 2H, H-5).

$^{13}$C-NMR (150 MHz, $D_2O$): δ [ppm]=156.8 (C-19); 81.1 (C-22); 65.1 (C-13); 62.9 (C-15); 51.5 (C-26 and C-27); 49.4 (C-3); 48.2 (C-17); 34.5 (C-1); 29.9-29.3 (C-5 to C-10); 28.8 (C-23, C-24 and C-25); 26.9 (C-4); 26.5 (C-12); 22.8 (C-11) and 19.0 (C-16).

ESI-MS: (m/z) calc. for $C_{22}H_{46}N_2O_5S$ $(M+H)^+$ 451.3200, ascertained 451.3214.

IR (neat): υ [$cm^{-1}$]=3456; 2973; 2925; 2855; 1680 (C═O); 1165 (C—O); 1035 (S═O), 606 and 521.

Example 14

Preparation of 3-(dimethyl(11-(methylamino)undecyl)ammonio)propane-1-sulfonate 3-((11-((tert-butoxycarbonyl)(methyl)amino)undecyl)dimethylammonio)-propane-1-sulfonate (600 mg, 1.33 mmol) was dissolved in ultrapure water (13 mL). The reaction vessel was rinsed with nitrogen and the solution was heated to 135° C. in the microwave for 90 minutes. The water was removed by lyophilization and the product was present as a colorless, strongly hygroscopic solid.

Yield: 93%

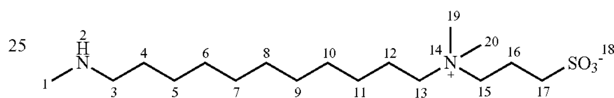

$^1$H-NMR (400 MHz, $D_2O$): δ [ppm]=4.79 ($D_2O$); 3.51-3.46 (m, 2H, H-15); 3.36-3.32 (m, 2H, H-13); 3.12 (s, 6H, H-19 and H-20); 3.01 (t, 2H, J=7.2 Hz, H-17); 2.95-2.91 (m, 2H, H-3); 2.63 (s, 3H, H-1); 2.28-2.20 (m, 2H, H-16); 1.81-1.77 (m, 2H, H-12); 1.69-1.61 (m, 2H, H-4); 1.39 (m, 4H, H-5 and H-11) and 1.33 (m, 10H, H-6 to H-10).

$^{13}$C-NMR (100 MHz, $D_2O$): δ [ppm]=64.2 (C-13); 61.9 (C-15); 50.6 (C-19 and C-20); 49.5 (C-3); 47.3 (C-17); 33.0 (C-1); 28.4-28.1 (C-6 to C-10); 26.0 (C-4); 25.7-25.4 (C-5 and C-11); 21.7 (C-12) and 18.1 (C-16).

ESI-MS: (m/z) calc. for $C_{17}H_{39}N_2O_3S$ $(M+H)^+$ 351.2676, ascertained 351.2689.

IR (neat): υ [$cm^{-1}$]=2919; 2849; 1196 (S═O); 1036 (S═O), 603 and 526.

Example 15

Formation of Dithiocarbamate

The formation of dithiocarbamate was monitored by absorption spectroscopy in the range of 230-400 nm. For this purpose, 1 mL of a 25 mM solution of the amine according to example 3 or example 14 and 500 μL of a 0.66 M solution $CS_2$ were prepared in MeOH. For the reference measurements of the starting substances, 10 μL each of the stock solutions were diluted with 1.5 mL MeOH in a UV semi-micro cuvette and the absorption was measured. To monitor the dithiocarbamate formation, 38 μL of the $CS_2$ solution were added to the remaining amine solution and the absorption was monitored over a period of 40 and 110 minutes, respectively. For this purpose, 10 μL of the reaction mixture were diluted with 1.5 mL MeOH after different time intervals and measured at the absorption spectrometer. As soon as the characteristic absorption maxima at 255 and 291 nm did not increase any more, the dithiocarbamate formation was completed and the ligand solution was used in the next step.

Example 16

Ligand Exchange

Prior to the ligand exchange, the QDQRs (1 nmol) were precipitated three times with MeOH and centrifuged at 6,700×g. The colorless supernatant was discarded and the nanoparticles were absorbed in 2.5 mL n-hexane. Furthermore, dilutions of the zwitterionic amines according to example 3, example 14, example 6 and example 8 (each 0.2 M) as well as of $CS_2$ (0.66 M) were prepared in MeOH. The ligand surpluses varied between 10,000 and 100,000 related to the concentration of nanoparticles, and the ratio of amine to $CS_2$ was 1:1. To form the dithiocarbamate ligands, the corresponding amounts of amine and $CS_2$ were filled up to a total volume of 1 mL with MeOH and stirred at room temperature for 15 minutes (for the amines according to example 3, 14 and 8) or 90 minutes (for the amine of example 6). The ligand solution was then added to the nanoparticles in n-hexane and the two-phase system was vigorously stirred for 30 minutes until the QDQRs precipitated from the reaction solution. In some cases, an extended reaction time of up to six hours was necessary to achieve precipitation of the nanoparticles. After short centrifugation (1 minute at 1,000×g), the now colorless organic phases were removed, the nanoparticles were carefully dried in a nitrogen stream and then incorporated in ultrapure water (0.5-1 mL).

Example 17

Stability Measurements

The following pH buffers were prepared for the stability measurements:

Citrate Buffer pH 5.1

Citric acid (960 mg, 5 mmol) was weighed in a 50 mL graduated flask, dissolved in ultrapure water (approx. 40 mL) and adjusted to a pH value of 5.1 using 1 M NaOH. Then it was filled up to the mark with ultrapure water (concentration: 0.1 M).

Phosphate Buffer pH 7.4

PBS buffer with a pH value of 7.4 was purchased commercially.

Borate Buffer pH 9.0

$H_3BO_3$ (62 mg, 1 mmol) was weighed in a 50 mL graduated flask, dissolved in ultrapure water (approx. 40 mL) and adjusted to a pH value of 9.0 using 1 M NaOH. Then it was filled up to the mark with ultrapure water (concentration: 20 mM).

Phosphate Buffer pH 11.5

$K_2HPO_4$ (8.71 g, 50 mmol) was weighed in a 50 mL graduated flask and dissolved in a small amount of ultrapure water. Subsequently, it was filled up to the mark with ultrapure water (concentration: 1 M). From this solution, 500 μL were diluted with 49.5 mL ultrapure water (concentration 0.01 M) and a pH value of 11.5 was adjusted using 1 M NaOH.

Furthermore, the following media were used for the stability measurements: 10 mM HEPES, DMEM (without phenol red), 10% FCS in DMEM, PBS and 1% BSA in PBS.

For the stability measurements, 990 μL of the pH buffer or medium were put in a quartz cuvette and 10 μL of the nanoparticle solution were added (final concentration: 20 nM). After an incubation period of two minutes, the fluorescence intensity of the samples was measured every 20 minutes within the first two hours, hourly in the further course of the day and thereafter every 24 hours. On the whole, the fluorescence intensity was monitored over a period of one week. The measurements were performed at an excitation wavelength of 350 nm.

Example 18

Cell Culture Experiments

The culture medium consisted of 10% FCS in DMEM with 1% PenStrep and sodium pyruvate in each case. The incubation of the cells always took place at 37° C. and a $CO_2$ content of 5%.

The zwitterionic Quantum Dots/Quantum Rods (QDQRs) nanoparticles were examined in various in vitro experiments with regard to their toxicity and non-specific cell uptake. Yellow-emitting QDQRs comprising the short- and long-chain zwitterionic ligand (QDQRs-17a and QDQRs-17b) were used for the studies to investigate a possible influence of the chain length of the ligand on the interactions of the QDQRs with cells. A549 cells were used for both toxicity and cell uptake studies. A549 cells are human basal epithelial cells derived from an adenocarcinoma of the lung which have been cultured as a cell line.

For the use of nanoparticles in biochemistry or medicine, it is essential that they do not produce intolerable toxicity. In the case of cadmium-containing nanoparticles, there is the general possibility that the cells may be damaged by escaping cadmium ions. The probability that cadmium ions are released into the environment is relatively high, especially with the QDQRs used here. On the one hand, the proportion of cadmium in the elongated nanoparticles is higher by a factor of 12 compared to spherical particles of the same diameter. On the other hand, the QDQRs lack a passivating shell of zinc sulfide, which is often used to coat cadmium-containing nanoparticles to prevent cadmium ions from leaching out.

The toxicity of the zwitterionic QDQRs-17a and QDQRs-17b was tested using the Cellomics Array Scan. For the toxicity tests, A549 cells were plated on a 96-well plate and incubated with QDQR solutions in a concentration range of 25 to 500 nM. Cadmium chloride, which was used in a concentration range from 25 to 1,000 μM, was used as the positive control. The increase in the cadmium chloride concentration by a factor of 1,000 is due to the fact that a single QDQR of the tested samples contains about 8,200 cadmium atoms. Assuming that the totality of the nanoparticles dissolve and release the cadmium contained in them, the lowest concentration of 25 nM QDQRs used would correspond to a concentration of 205 μM cadmium chloride. After an incubation period of 16 hours, the cells were blended with a staining solution consisting of the cell nucleus dye Hoechst 33342 and the mitochondrial dye MitoTracker® Deep Red FM and then fixed with formaldehyde solution. The 96-well plates were then read out with the Cellomics Array Scan. A software was used to automatically determine the parameters number of cells, cell nucleus intensity and cell nucleus size using the intensity of the dye by Hoechst, and the transmembrane potential of the mitochondria on the basis of the mitochondrial dye. In addition, microscopic images of the cells were taken to control the number of cells and cell morphology.

Example 19

Toxicity Tests

For the toxicity tests, A549 cells were plated in culture medium on a 96-well plate (10,000 cells per well) and incubated overnight. When the medium had been sucked off, the samples to be tested (diluted with culture medium, 100

μL per well) were applied in different concentrations and incubated for 16 hours. The samples were then removed and the cells were mixed with 100 μL staining solution (final concentration: 75 nM MitoTracker® Deep Red and 2.5 g/ml Hoechst 33342 in DMEM with 10% FCS) and incubated for a further 30 minutes. To fix the cells, the staining solution was removed and 100 μL of a warm fixing solution (3.7% formaldehyde in Dulbecco's PBS, DPBS) were added. After 20 minutes, the fixing solution was sucked off and washed twice with DPBS before the samples were measured on the Cellomics Array Scan.

FIG. 1 shows a quantification of the toxicity test of the QDQRs-17a and QDQRs-17b as well as cadmium chloride (with (A) number of cells, (B) intensity of the cell nucleus dye Hoechst 33342, (C) size of the cell nuclei and (D) transmembrane potential of the mitochondria; explanatory note: Since cadmium chloride shows a toxic effect on the cells already starting at a concentration of 100 μM, only the values up to 500 μM are shown in the illustration).

FIG. 1 shows the above parameters depending on the concentration of QDQRs or cadmium chloride used. Each data point represents the mean value of three measured values. The diagrams A to D in FIG. 1 clearly show that both QDQRs-17a and QDQRs-17b, including the highest tested concentration of 500 nM, have no discernible toxic effect on the cells. The number of cells per well (A), the cell nucleus intensity (B), the cell nucleus size (C) and also the transmembrane potential of the mitochondria (D) remain almost constant over the entire concentration range.

Figure 2:
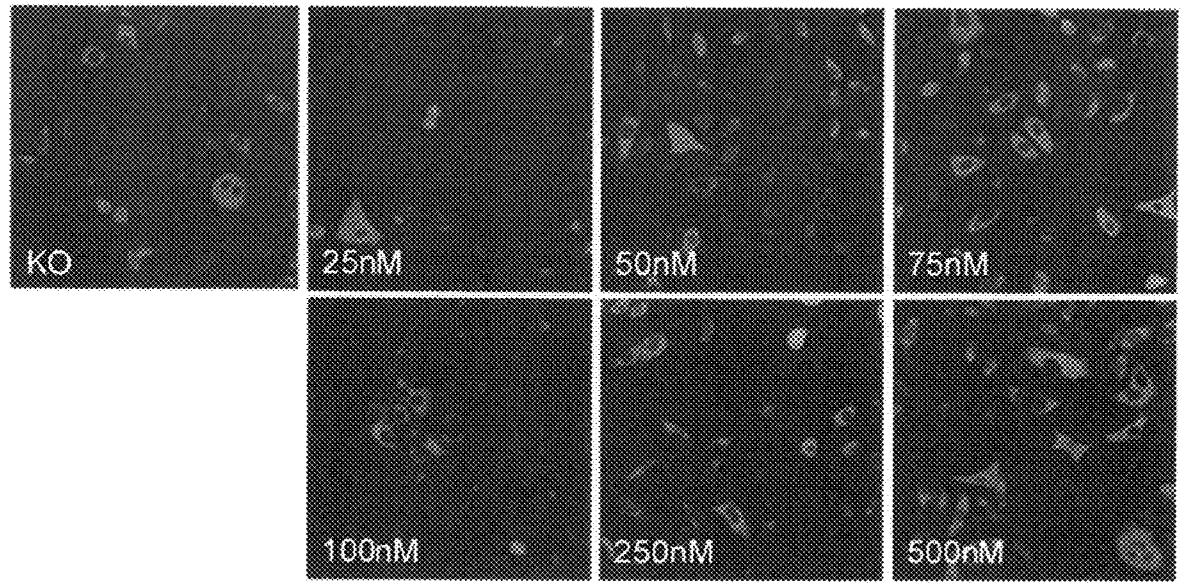

Similarly, no morphological changes of the cells or cell nuclei after 16 hours of incubation with zwitterionic QDQRs are discernible in the microscopic images. As an example, the microscopic images of the A549 cells after incubation with QDQRs-17a are shown in FIG. 2. The self-fluorescence of the QDQRs cannot be seen in the images because it was suppressed by appropriate filter settings on the device.

FIG. 2 shows microscopic images of the A549 cells after 16 hours incubation with different concentrations of QDQRs-17a. The cell nuclei are stained with Hoechst 33342 (blue) and the mitochondria with MitoTracker® Deep Red (red). As a control (KO), an image of A549 cells incubated without QDQRs is shown after 16 hours.

In contrast, cadmium chloride at a concentration of 100 μM or more, which corresponds approximately to a QDQR concentration of 12 nM or more, has a toxic effect on the cells. The number of cells per well, the cell nucleus intensity and the cell nucleus size decreases significantly due to cell death (FIG. 1 A-C). The transmembrane potential first increases in the concentration range from 50 to 100 μM and then decreases again (FIG. 1D). This process is typical for the toxic effect of a substance. Cell stress releases apoptosis-triggering factors and initially there is an increase in mitochondrial mass, which in the measurement leads to an increase in the intensity of the mitochondrial dye. If the cadmium chloride concentration is further increased, the cells die increasingly, whereby the mitochondrial mass also decreases and the signal of the dye becomes weaker again. The renewed increase of cell nucleus intensity and cell nucleus size at a concentration of 500 μM cadmium chloride as well as the large error bars of these measured values can be explained by the fact that at high toxicity of a substance only very few cells are still present in the well, whereby fewer measuring points are available for the evaluation and the statistical errors become correspondingly large.

Figure 3:
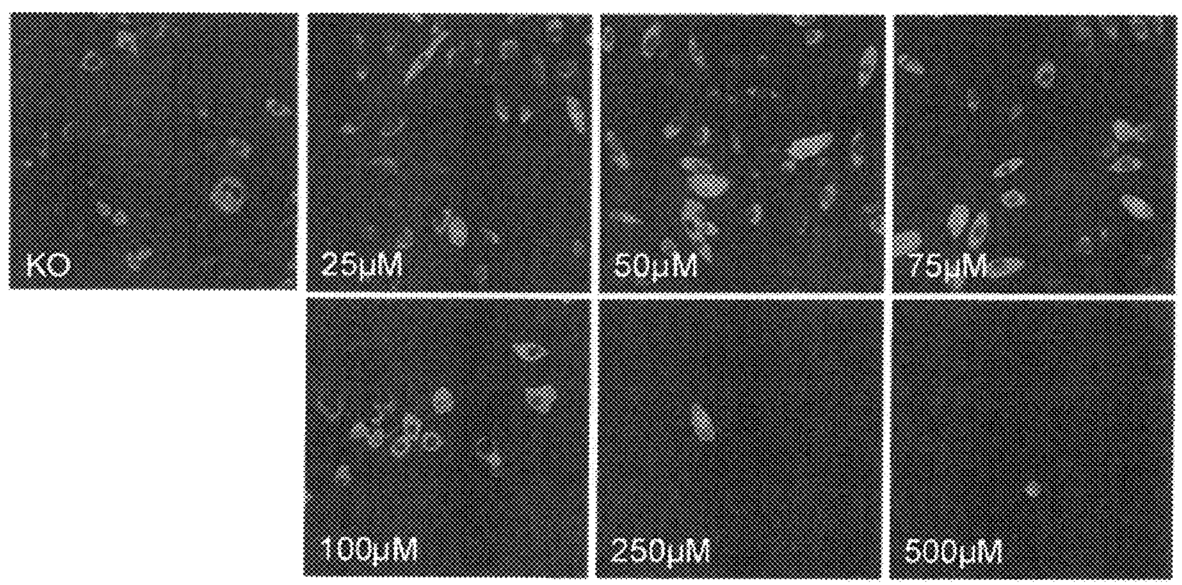
FIG. 3 shows microscopic images of the A549 cells after 16 hours incubation with different concentrations of cadmium chloride.

This becomes particularly clear when looking at the microscopic images of the cells after 16 hours of incubation with cadmium chloride, which are shown in FIG. 3. At a concentration of 100 μM cadmium chloride or more, the number of cells decreases noticeably and they get globular. At higher concentrations of cadmium chloride only a few cells can be found in the wells.

FIG. 3 shows microscopic images of the A549 cells after 16 hours of incubation with different concentrations of cadmium chloride. The cell nuclei are stained with Hoechst 33342 (blue) and the mitochondria with MitoTracker® Deep Red (red). As a control (KO), an image of A549 cells incubated without cadmium chloride is shown after 16 hours.

In summary, it can be said that despite the high cadmium content in the QDQRs used and the absence of an additional passivating zinc sulfide case, there is no measurable toxicity originating from the QDQRs up to a concentration of 500 nM. Thus, the zwitterionic QDQRs produced fulfil an important prerequisite for later biomedical applications.

Thus, it could be shown that zwitterionic QDQRs have no toxic effect on A549 cells even in high concentrations of up to 500 nM.

Next, the uptake behavior of the QDQRs-17a and QDQRs-17b with A549 cells was analyzed and it was examined whether the nanoparticles were accommodated in different ways depending on the chain length of the ligand.

Example 20

Cell Uptake Experiments with A549 Cells (In Vitro)

For the cell uptake experiments, A549 cells were plated in culture medium on an 8 well Labtek (20,000 cells per well) and incubated for 24 and 48 hours, respectively. The medium was sucked off and the samples to be investigated (diluted with DMEM and correspondingly with or without 10% FCS, concentration: 100 nM) were added. The cells were then incubated for four and 16 hours, respectively. After expiry of the incubation period, the medium was removed, the cells were blended with a staining solution (final concentration: 2.5 μg/ml Hoechst 33342 in DMEM, 200 μL per well) and incubated again for 30 minutes. Here again, the cells were fixed with a 3.7% formaldehyde solution in DPBS for 20 minutes. After washing the cells twice with DPBS, the samples were measured with a confocal microscope.

On the one hand, two different incubation times (four and 16 hours) were tested. On the other hand, incubation was performed either in the presence or absence of 10% FCS. The absence of FCS in the medium was used to investigate whether nanoparticle uptake into the possibly famishing cells could be forced. In all experiments the cells were incubated with a 100 nM QDQR solution. After incubation, the cells were washed, the cell nuclei stained with Hoechst 33342, fixed and analyzed with a confocal microscope.

Figure 4:
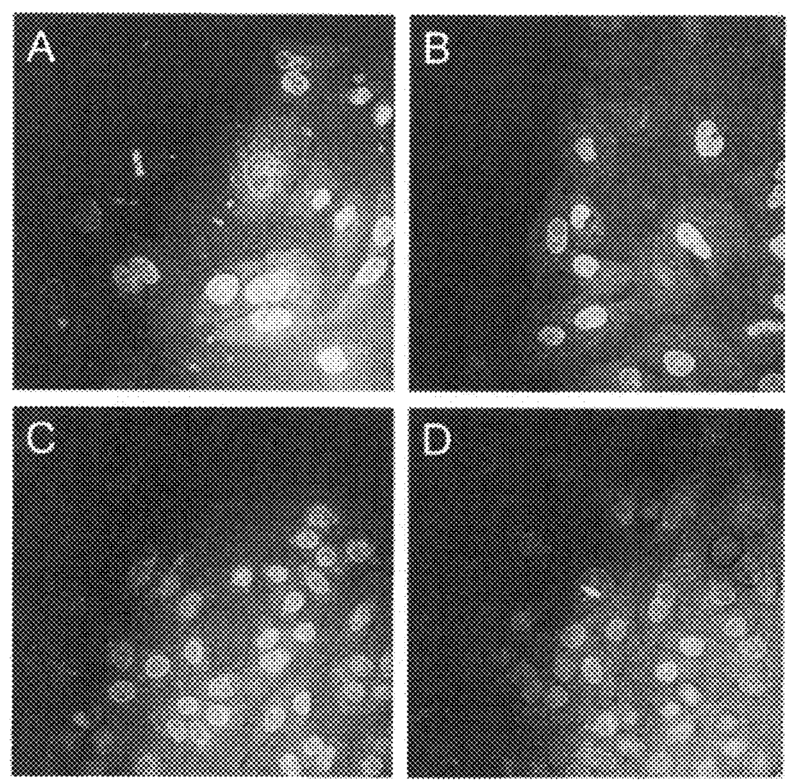
FIG. 4 shows confocal microscopic images of A549 cells after incubation.

For QDQRs-17a, an unspecific uptake of the nanoparticles was visible under all experimental conditions, see FIG. 4. The uptake after four hours (A and B) was not as pronounced as after 16 hours (C and D). Moreover, after four hours of incubation, the QDQRs were mainly located near the cell membrane, whereas the nanoparticles were more or less evenly distributed inside the cell after a longer incubation period. The fluorescence of the nanoparticles could often be detected in punctiform structures, which are presumably endosomes filled with QDQRs. Since A549 cells are no phagocytic cells, QDQRs most likely enter the cells via unspecific endocytosis. In addition, after four hours of incubation in the presence of 10% FCS (B), the QDQRs were absorbed significantly less by the cells as compared to the experiment under serum-free condition (A). A reduced uptake of nanoparticles in serum-containing medium is already known from literature, whereby the reduced uptake is attributed to the presence of a protein corona. Although zwitterionic ligands on nanoparticles are supposed to prevent the formation of a protein corona, the zwitterionic QDQRs-17a seem to interact with the protein in solution, resulting in reduced cell uptake.

FIG. 4 shows confocal microscopic images of A549 cells after incubation with 100 nM QDQRs-17a for four hours (A and B) and 16 hours (C and D). Incubation was performed under serum-free conditions (A and C) or in the presence of 10% FCS (B and D). The cell nuclei were stained with the dye Hoechst 33342 (blue). The red areas result from the fluorescence of the QDQRs.

Figure 5:
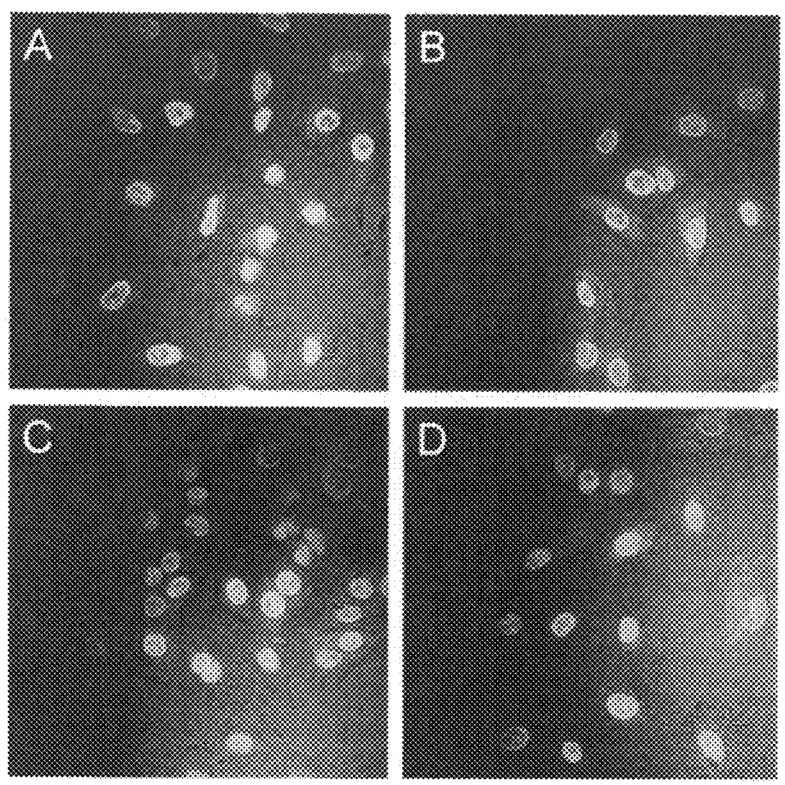
FIG. 5 shows confocal microscopic images of A549 cells after incubation with 100 nM QDQRs-17b.

The incubation of A549 cells with QDQRs-17b surprisingly showed a completely different picture (see FIG. 5).

FIG. 5 shows confocal microscopic images of A549 cells after incubation with 100 nM QDQRs-17b for four hours (A and B) and 16 hours (C and D). Incubation was performed under serum-free conditions (A and C) or in the presence of 10% FCS (B and D). The cell nuclei were stained with the dye Hoechst 33342 (blue). The red areas result from the fluorescence of the QDQRs.

After an incubation period of four hours, the nanoparticles were absorbed by the cells neither under serum-containing conditions (B) nor under serum-free conditions (A). Also the increased incubation time of 16 hours in the presence of 10% FCS did not result in an unspecific uptake of QDQRs (D). Only in serum-free medium, a slight unspecific uptake of QDQRs was detectable (C), which, however, was significantly lower compared to QDQRs-17a.

In general, the cell uptake of nanoparticles depends on many different factors, such as the size and shape of the particles, their surface charge, or the presence of a protein corona. As could be demonstrated by the DLS measurements and TEM images, both the size and shape of QDQRs-17a and QDQRs-17b are almost identical, so that these factors cannot explain the different cell uptake behavior.

In summary, it can be said that QDQRs are different from A549 cells in their uptake behavior in a surprisingly high extent. Thus, the zwitterionic ligands on the nanoparticle surface are suitable for influencing cell uptake by structural changes.

In Vivo Studies

For the in vivo experiments, 12 week old FVB mice were anesthetized by inhalation of 4% isoflurane. During the experiments, anesthesia was maintained by inhalation of 1-1.5% isoflurane. For intravital microscopy, the liver and the intestinal tract of the mouse were exposed under anesthesia and attached to a cover glass. In order to avoid hypothermia of the mouse, the experiments were performed in an air-conditioned chamber at a temperature of 32° C. The visualization of the nanoparticle uptake was performed using a confocal microscope equipped with a resonant scanner (Nikon AIR). 150 μL of a 10 μM QDQR solution in sterile, physiological NaCl was administered intravenously to the mouse and the uptake of the nanoparticles was followed with a sampling rate of 30 images per second. In addition, images of the liver were taken before and after QDQR injection. To mark the macrophages, green-emitting FluoSpheres® made of polystyrene (~$10^8$ particles/mouse) with a size of about 1 μm were also administered intravenously 15 minutes after injection of the QDQRs.

FluoSpheres® are microspheres (also called latex beads or latex particles) which are present in colloidal dimensions and formed from an amorphous polymer such as polystyrene. To track biological events, they may be loaded or labelled with chromophores, in particular fluorescent dyes.

To study the uptake into other tissues, the mouse was perfused with 4% paraformaldehyde in PBS 15 minutes after the QDQRs were injected. After removal of lung, spleen, kidney and interscapular brown fatty tissue, the tissues were immediately analyzed microscopically.

After perfusion of the mouse, 200 μm thick liver sections were prepared using a VT1000S microtome (Leica) for immune staining. The sections were washed with PBS and incubated with 5% glycine in PBS for 30 minutes to reduce auto-fluorescence. Subsequently, the sections were blocked and permeabilized for two hours in 3% BSA and 0.3% Triton X-100 (both in PBS). After washing the sections again, they were incubated for 48 hours at 4° C. with the primary antibody (rat-anti-mouse CD31, 1:500 in 1% BSA). The sections were then washed three times with PBS for 10 minutes each and incubated overnight at 4° C. with the secondary antibody (anti-rat Cy5, 1:500 in 1% BSA). The sections were washed again three times with PBS and the cell nuclei stained with DAPI. The analysis of the sections was performed with a confocal microscope (Nikon AIR).

Example 21

Uptake and Organ-Related Distribution of QDQRs-17a and QDQRs-17b In Vivo

In principle, after intravenous injection of nanoparticles, a distinction can be made between three different mechanisms that remove the nanoparticles from the bloodstream again. The excretion can take place through the kidneys with urine (renal) or through the liver with bile (hepatobiliary). In addition, the nanoparticles can be removed by absorption in macrophages of the reticuloendothelial system (RES, liver, spleen or bone marrow).[3] The liver is one of the main organs through which various nanoparticles are absorbed and, if necessary, excreted again.[4,5] In the liver, mainly the so-called Kupffer cells, i.e. macrophages especially found in the liver, are responsible for the uptake of larger particles.[6,7] It is also known from literature that in addition to the Kupffer cells, the sinusoidal liver endothelial cells (LSECs) can also internalize nanoparticles.[8,9] Therefore, the behavior of zwitterionic QDQRs was observed in real time by means of intravital microscopy in the liver of mice and the organ-related distribution of the nanoparticles was analyzed ex vivo. Each mouse got an injection of 1.5 nmol QDQRs in physiological saline solution (150 μL) into the tail vein in each experiment. Considering the blood volume of a mouse of about 3 mL, this amount corresponds to a QDQR concentration of about 500 nM in the organism. Up to this concentration, no toxic effects of the QDQRs could be observed in the in vitro studies (cf. example 19), which is why this concentration was also used in the in vivo experiments.

After the intravenous injection of the QDQRs with the short-chain zwitterionic ligand 17a, a so-called lining of the blood vessels in the liver through the nanoparticles was visible, which speaks for an uptake into LSECs. In addition to the lining, the QDQRs were present in more densely packed, larger structures, indicating an uptake in Kupffer cells (see FIG. 6, left side). The QDQRs with the long-chain zwitterionic ligand 17b also showed a lining of the blood vessels. In contrast to QDQRs-17a, however, no larger accumulations of nanoparticles could be detected (see FIG. 6, right side). Thus, the different behavior of QDQRs-17a and QDQRs-17b in vitro is also reflected in the in vivo findings. Since the QDQRs were absorbed in the liver, also the intestine as an organ with strong blood supply and high immune cell activity was examined intravitally and microscopically. In contrast to the liver, there was no unspecific uptake of the nanoparticles in the intestine.

Figure 6:
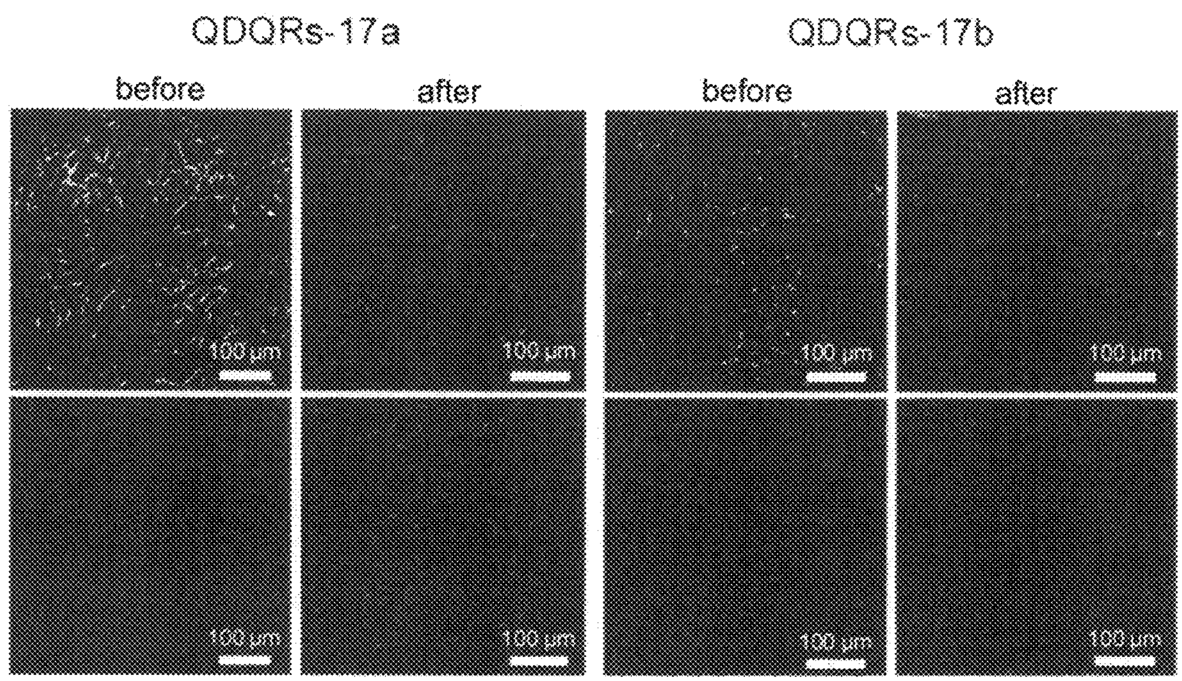
FIG. 6 shows intravital microscope images of the liver before and after injection of QDQRs-17a and QDQRs-17b.

FIG. 6 shows microscopic images of the liver before and after the injection of QDQRs-17a (left side) and QDQRs-17b (right side). Upper row: Superposition of the background signal and the channel in which the fluorescence of the QDQRs (red areas) is measured. Lower row: Channel in which the fluorescence of the QDQRs is measured.

Example 22

Co-Injection of QDQRs-17a and QDQRs-17b and FluoSpheres® In Vivo

Figure 7:
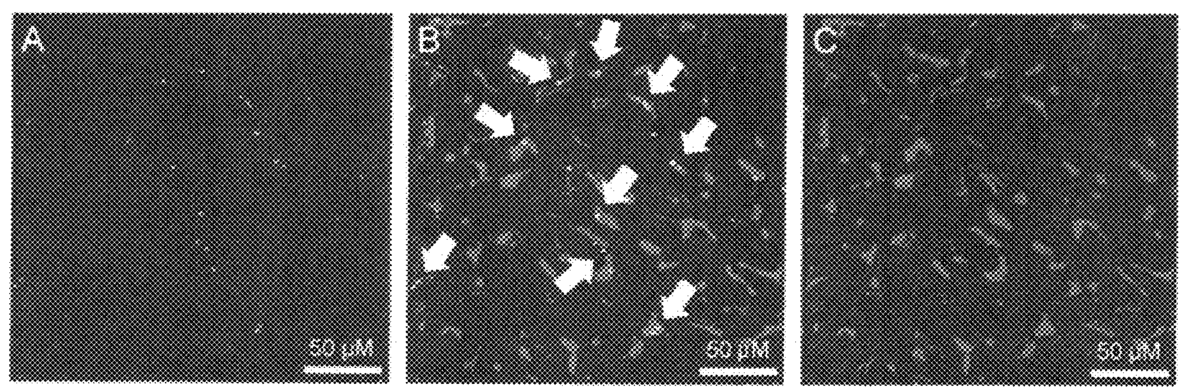
FIG. 7 shows intravital microscopic images of a liver section after co-injection of QDQRs-17a or QDQRs-17b and FluoSpheres®.

In order to obtain information about the larger structures in the liver in which QDQRs 17a accumulated, FluoSpheres® about 1 μm in size were injected in another experiment after injection of the QDQRs. Due to their size, the particles which likewise have a fluorescent effect accumulate exclusively in phagocytes such as Kupffer cells, but not in LSECs.[10] FIG. 7 shows a microscopic image of a liver section after injection of QDQRs-17a and FluoSpheres®. The fluorescence of the FluoSpheres® is shown in green (A) and the fluorescence of the QDQRs is shown in red (C). FIG. 7B shows the superposition of the two images. A co-localization of the QDQRs and the FluoSpheres® within the same structures can be clearly seen, which speaks for an uptake of the QDQRs-17a into the Kupffer cells of the liver.

FIG. 7 shows a microscopic image of a liver section after injection of QDQRs 17a and FluoSpheres®. The fluorescence of the FluoSpheres® is shown in (A), the superposition of the fluorescence of FluoSpheres® and QDQRs-17a in (B), and the fluorescence of QDQRs-17a in (C). The arrows in (B) mark the structures in which both FluoSpheres® and QDQRs-17a are present.

Example 23

Immunohistological Examination of Tissue Sections Ex Vivo

The lining of the blood vessels after injection of QDQRs-17a and QDQRs-17b suggests, as already mentioned, an uptake of the nanoparticles into LSECs. To confirm this assumption, the mice were perfused after the experiments and vibratome sections of the liver were made, which were immunohistologically examined. To this end, the sections were first incubated with a primary antibody (rat anti-mouse CD31) and then with a secondary antibody (anti-rat Cy5) to mark the liver endothelium. In addition, the cell nuclei were stained with the fluorescent dye 4',6-diamidine-2-phenylindole (DAPI). The analysis of the liver sections was performed with a confocal microscope. FIGS. 8A-C show microscopic images of a liver section of a mouse which got an injection with QDQRs-17a. The fluorescence of the QDQRs is shown in red (A) and the endothelial marker in violet (C). The cell nuclei are stained blue by the dye DAPI and are used for orientation. The superposition of the two images (B) shows that the QDQRs are partially located in the hepatic endothelial cells, since the violet staining (endothelial markers) and the fluorescence of the QDQRs overlap in some places. In addition, these images again show the uptake of QDQRs-17a in Kupffer cells (larger structures in red). FIGS. 8D-F show the microscopic images of a liver section of a mouse which got an injection with QDQRs-17b. Again, the superposition (E) of the fluorescence of the QDQRs and the endothelial marker shows the overlapping of red and violet areas. It can therefore be assumed that the QDQRs are incorporated into LSECs.

Figure 8:
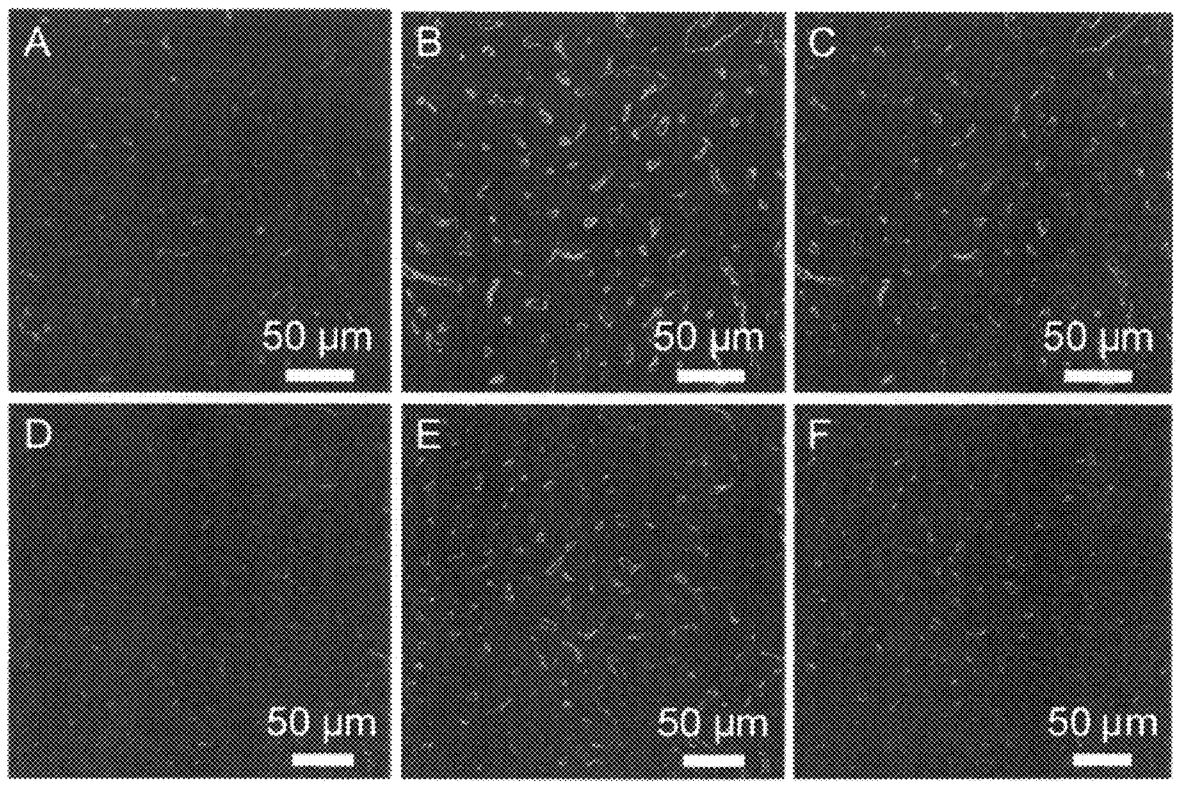
FIG. 8 shows intravital microscopic images of a liver section after the injection of QDQRs-17a or QDQRs-17b and histological staining with an endothelial marker.

FIG. 8 shows microscopic images of a liver section after injection of QDQRs-17a (A-C) or QDQRs-17b (D-F). The fluorescence of the QDQRs is shown in red (A and D), the hepatic endothelium is marked with CD31 and shown in violet (C and F) and the cell nuclei are stained with DAPI (blue). The images B and E show the superposition of QDQRs and endothelial markers.

Example 24

Organ-Related Distribution of QDQRs-17a and QDQRs-17b Ex Vivo

Figure 9:
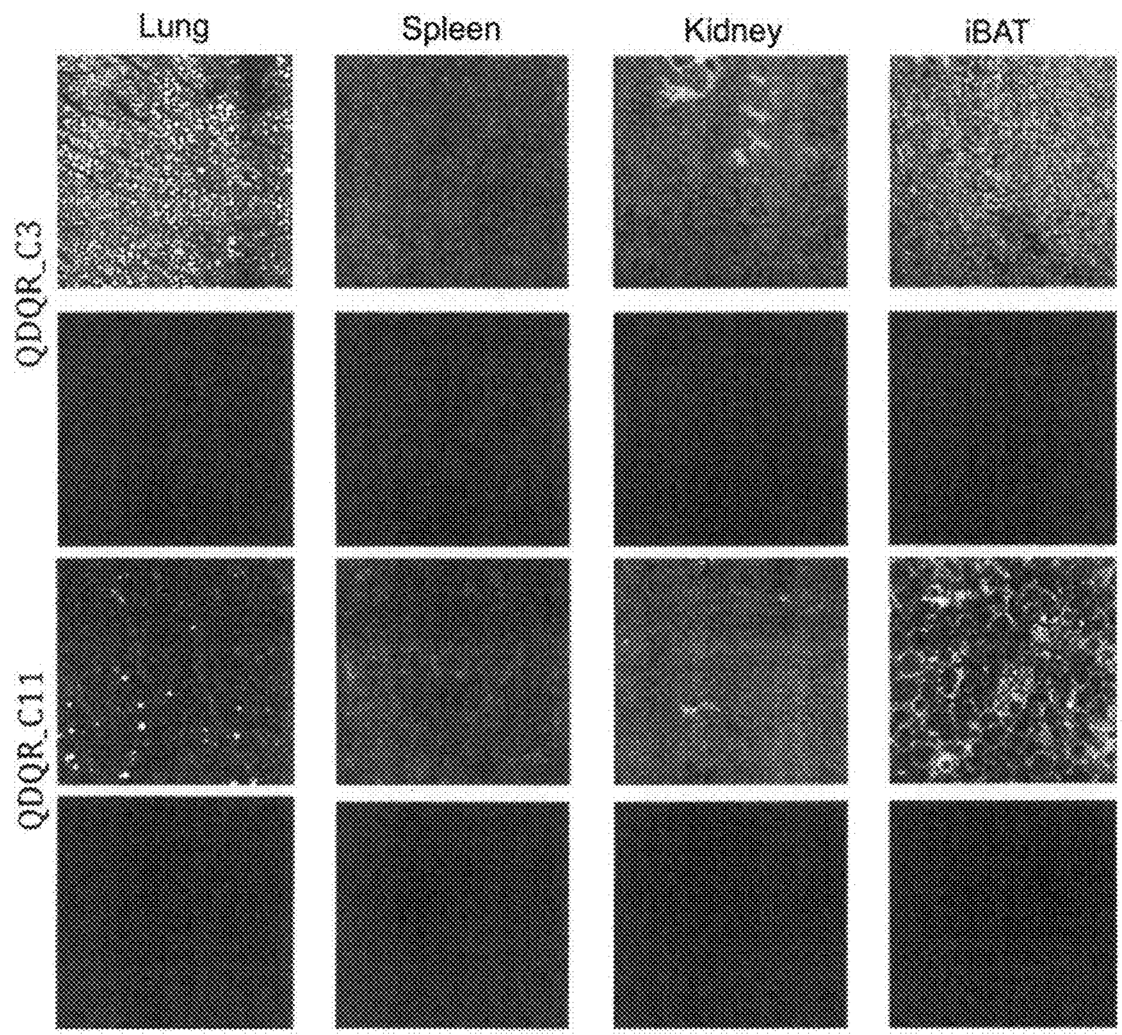
FIG. 9 shows microscopic images of QDQRs-17a and QDQRs-17b in different tissues of lung, spleen, kidney and interscapular brown fatty tissue.

After analyzing the behavior of QDQRs in the liver by intravital microscopy and confirming the uptake of nanoparticles into LSECs and/or Kupffer cells by further experiments, the organ-related distribution of QDQRs was examined ex vivo. After perfusing the mice, the lung, spleen, kidneys and interscapular brown fat tissue (i-BAT) were dissected and again microscopically analyzed. FIG. 9 shows microscopic images of QDQRs 17a and QDQRs 17b in different tissues of lung, spleen, kidney and interscapular brown fatty tissue. The QDQRs 17b showed no uptake in the investigated tissues. In contrast, QDQRS-17a was ingested in both the lung and the spleen, but the signal of the nanoparticles in these organs was much lower compared to the liver. The observations from the in vivo experiments therefore correspond with the results from the in vitro studies in which QDQRs-17a showed an unspecific uptake in A549 cells, whereas QDQRs-17b were incorporated only under drastic conditions (long incubation times and without addition of FCS).

QDQRs-17b therefore open up interesting therapeutic perspectives, as they are mainly taken up into LSECs only but not in Kupffer cells. It is known from literature that LSECs play an important role in peripheral immune regulation by regulatory T cells.[11]

Nanoparticles that are specifically absorbed by LSECs can, for example, be coupled with certain autoantigen peptides. By nanoparticle-mediated targeting, LSECs can process and present these autoantigen peptides. Carambia et al. showed that this leads to an induction of regulatory T cells (Tregs) that recognize the autoantigen.[1] Tregs act as immunomodulators. They can attenuate immune responses and thus contribute to tolerance with respect to antigens.

In a mouse model of multiple sclerosis (MS), nanoparticles were injected to which peptides of the myelin basic protein were coupled. This resulted in an induction of specific Tregs which were able to suppress MS progression.[1] This effect depended solely on the induction of the Tregs by the LSECs. Thus, QDQRs-17b might be a way to transport substances specifically into LSECs to mediate immunoregulatory effects. These substances may include peptides or also other biologically active molecules such as inhibitors of intracellular signal pathways that have an immunomodulatory effect.

Example 25

Synthesis of 2-((11-bromoundecyl)oxy)tetrahydro-2H-pyran

According to Yang, C.[12], 11-bromoundecan-1-ol (10.67 g, 41.6 mmol, 1 eq.) was dissolved in MTBE (94 mL, 0.80 mol, 19.2 eq.) and DHP (10.27 mL, 117 mmol, 2.81 eq.) was added. After stirring briefly at room temperature (RT), p-TsOH (53 mg, 308 μmol, 0.007 eq) was slowly added as a catalyst and stirred for four hours at RT.

Thin layer chromatography (DC) with Hex:EtOAc 19:1 showed a reaction. In a micro-preparation (2 mL), it was washed with a $Na_2CO_3$ solution (4 mL) was washed to neutralize p-TsOH, dried over $Na_2SO_4$ and concentrated to dryness. The $^1$H-NMR spectrum was consistent with the target structure. Therefore, the batch was fully processed by washing three times with $Na_2CO_3$ solution, washing once with $H_2O$, drying over $Na_2SO_4$ and concentration to dryness. The product was obtained as a colorless oil with a yield of 94%. The spectroscopic data corresponded to the literature. [13]

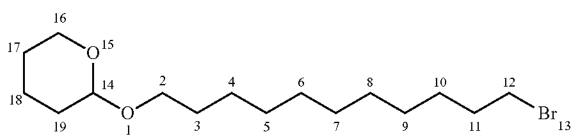

$^1$H-NMR (400 MHz, $CDCl_3$, 27° C., TMS): δ [ppm]=4.57-4.49 (m, 1H, H-14); 3.86-3.76 (m, 1H, H-16); 3.72-3.62 (dt, $J^3$=9.6, 6.9 Hz, 1H, H-16); 3.49-3.40 (m, 1H, H-2); 3.38-3.27 (m, 1H, H-2; 2H, H-12); 1.86-1.72 (m, 1H, H-18; 2H, H-11); 1.71-1.60 (m, 1H, H-19); 1.59-1.42 (m, 2H, H-17; 1H, H-18; 1H, H-19; 2H, H-3); 1.41-1.16 (m, 14H, H-4-H-10).

$^{13}$C-NMR (400 MHz, $CDCl_3$, 27° C., TMS): δ [ppm]=98.78 (C-14); 67.62 (C-2); 62.25 (C-16); 33.86 (C-12); 32.86 (C-11); 30.81 (C-19); 29.78 (C-3); 29.54 (C-7); 29.48 (C-6, C-8); 29.43 (C-5); 28.77 (C-9); 28.19 (C-10); 26.26 (C-17); 25.57 (C-4); 19.70 (C-18).

ESI-MS: (m/z) calc. for $C_{16}H_{31}BrO_2$ $(M+H)^+$ 334.1507, ascertained 339.1862.

IR (neat): $\tilde{\nu}$ [$cm^{-1}$]=2923 (C—H); 2853 (O—CH—O); 1077 (CH—O—CH).

Example 26

Synthesis of diethyl(11-hydroxyundecyl)phosphonate

According to Yang, C.[67], 2-((11-bromoundecyl)oxy)tetrahydro-2H-pyran (5.51 g, 14.9 mmol, 1 eq.) was dissolved in $P(OEt)_3$ (6 mL, 34.3 mmol, 2.3 eq.), reacted at 135° C. for ten hours (the reaction was monitored by DC in Hex:EtOAc 1:1) and then stirred at RT for a further ten hours. After removal of $P(OEt)_3$ by an oil pump, the $^1$H-NMR spectrum showed a very low conversion. Therefore, a small amount of the reaction solution (1 mL) was stirred with $P(OEt)_3$ (1.2 mL) at 165° C. in the microwave [MW] for one hour at a pressure of 4.4 bar. The reaction control by NMR again showed that the reaction had taken place. Then the complete batch (4.7 g) was reacted after the addition of $P(OEt)_3$ (5.2 mL) for 90 minutes at 165° C. with a pressure of 2.7 bar.

The reaction solution was freed from $P(OEt)_3$ at 70° C. under vacuum and purified by column chromatography (100 mL flash column [FS]; 50 g silica gel [KG]).

[100 mL Hex, 200 mL Hex:EtOAc 4:1, 300 mL Hex:EtOAc 7:3, 300 mL Hex:EtOAc 3:2, 500 mL 1:1 Hex:EtOAc, 200 mL 1:4 Hex:EtOAc, 100 mL EtOAc].

During column chromatography, the fractions were monitored by DC. Before combining the organic phases with the suspected product, they were checked separately by NMR. The $^1$H-NMR spectrum showed that a 1.2:1 product mixture of the desired product and diethyl(ethylphosphonate) was present. The spectroscopic data of the two substances corresponded to the literature.[14,15]

$^1$H-NMR (500 MHz, $CDCl_3$, 27° C., TMS): δ [ppm]=4.61-4.52 (t, $J^3$=3.6 Hz, 1H, H-

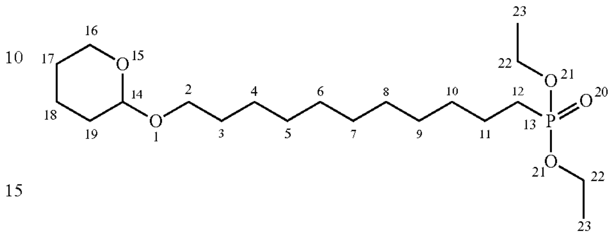

14); 4.20-3.98 (m, 4H, H-22); 3.90-3.80 (m, 1H, H-16); 3.77-3.66 (m, 1H, H-16); 3.54-3.43 (m, 1H, H-2); 3.43-3.30 (m, 1H, H-2); 1.90-1.64 (m, 1H, H-18; 2H, H-11; 1H, H-19); 1.63-1.44 (m, 2H, H-17; 1H, H-18; 1H, H-19; 2H, H-3); 1.40-1.24 (m, 6H, H-23; 14H, H-3-H-10).

$^{13}$C-NMR (500 MHz, $CDCl_3$, 27° C., TMS): δ [ppm]=98.97 (C-14); 67.81 (C-2); 62.48 (C-16); 61.51 (C-22); 30.81 (C-12); 29.87 (C-11); 29.66 (C-19); 29.59 (C-3); 29.48 (C-6, C-8); 29.21 (C-7); 26.36 (C-5); 25.63 (C-9); 22.51 (C-10); 19.84 (C-17); 19.51 (C-4); 18.38 (C-18); 16.59 (C-23).

ESI-MS: (m/z) calc. for $C_{20}H_{41}O_5P$ $(M+H)^+$ 392.2692, ascertained 309.2229 (fragment after elimination of DHP).

IR (neat): $\tilde{\nu}$ [$cm^{-1}$]=2981 (C—H); 2929 (C—H); 2856 (O—CH—O); 1247 ($R(R'O)_2P{=}O$); 1077 (CH—O—CH); 957 (P—O—$C_2H_5$).

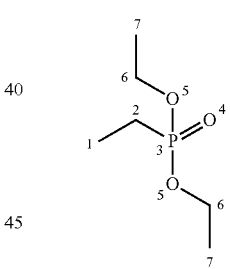

Diethyl(ethylphosphonate)

$^1$H-NMR (500 MHz, $CDCl_3$, 27° C., TMS): δ [ppm]=4.17-3.97 (m, 4H, H-6); 1.80-1.63 (dq, 3=18.3, 7.7 Hz, 2H, H-2); 1.34-1.24 (t, J=7.1 Hz, 6H, H-7); 1.20-1.06 (dt, 3=20.0, 7.7 Hz, 3H, H-1).

$^{13}$C-NMR (500 MHz, $CDCl_3$, 27° C., TMS): δ [ppm]=61.51 (C-6); 19.51 (C-2); 16.61 (C-7), 6.71 (C-1).

ESI-MS: (m/z) calc. for $C_6H_{15}O_3P$ $(M+H)^+$ 166.0759, ascertained 160.6168.

IR (neat): $\tilde{\nu}$ [$cm^{-1}$]=2982 (C—H); 2942 (C—H); 2233 ($R(R'O)_2P{=}O$); 1247 ($R(R'O)_2P{=}O$).

Amberlyst-15 H was used for the deprotection according to Azzouz, R.[16]. It was activated by rinsing with MeOH×2, H2O×2, HCl 1M×1, HCl semi-conc. ×1, $H_2O$ [up to pH=7]×4 and MeOH×2 {1×=20 mL}.

The product mixture was stirred for two hours at 45° C. in MeOH (10 mL). The $^1$H-NMR spectrum was consistent with the target structure. The desired product was obtained as a turbid colorless oil in an 83% yield. The spectroscopic data corresponded to literature. [64]

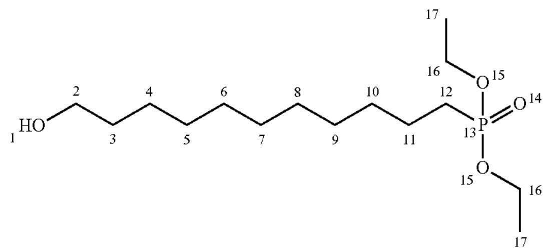

$^1$H-NMR (400 MHz, DMSO-d6, 27° C., TMS): δ [ppm]=4.59-4.02 (s br, 1H, H-1); 4.08-3.88 (m, 4H, H-16); 3.48-3.37 (t, J=6.5 Hz, 2H, H-2); 1.76-1.61 (m, 2H, H-12); 1.51-1.18 (m, 6H, H-17; 16H, H-3-H-10).

$^{13}$C-NMR (600 MHz, DMSO, 27° C., TMS): δ [ppm]=60.77-60.66 (C-2, C-16); 32.54 (C-3); 29.82 (C-11); 29.66 (C-7); 28.81 (C-6, C-8); 28.51 (C-5, C-9); 25.49 (C-10); 25.16 (C-4); 16.28 (C-17). C-12.

$^{31}$P-NMR (400 MHz, DMSO, 27° C., $H_3PO_4$): δ [ppm]=31.94 (P-13).

ESI-MS: (m/z) calc. for $C_{15}H_{33}O_4P$ $(M+H)^+$ 308.2116, ascertained 309.2199.

IR (neat): $\tilde{\nu}$ [cm$^{-1}$]=3418 (O—H); 2981 (C—H); 2926 (C—H); 2854 (—$CH_2$—); 1220 (R(R'O)$_2$P═O); 1022 (C—O); 955 (P—O—$C_2H_5$).

Example 27

Synthesis of diethyl(11-(trityloxy)undecyl)phosphonate

According to Rele, S.[17], a solution of 11-bromoundecane-1-ol (1.283 g, 5.01 mmol, 1 eq.) in DCM (12 mL, 188 mmol, 37.5 eq.) was cooled in an ice bath, mixed with $NEt_3$ (837 μL, 6.01 mmol, 1.2 eq.) before a solution of trityl chloride (1.577 g, 5.54 mmol, 1.1 eq.) in DCM (3 mL, 47 mmol, 9.4 eq.) was slowly added in drops. The ice bath was removed after 30 minutes. After four hours, the reaction was declared complete according to DC in Hex:EtOAc 9:1.

The triethylamine hydrochloride [$NEt_3$*HCl] formed during the reaction was filtered off.

The raw mixture was purified by column chromatography with Hex:EtOAc 19:1. The combined organic phases were concentrated to dryness.

The $^1$H-NMR spectrum was consistent with the target structure. The desired product was obtained as a turbid colorless oil with 70% yield.

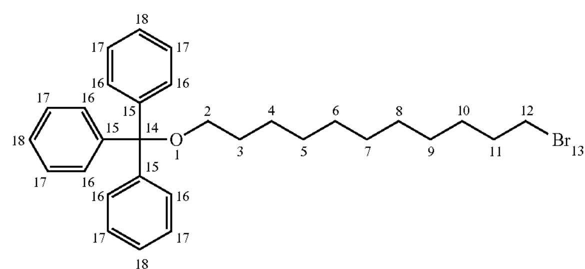

$^1$H-NMR (600 MHz, DMSO, 27° C., TMS): δ [ppm]=7.40-7.34 (d, J$^3$=8.0 Hz, 6H, H-16); 7.34-7.29 (t, J=7.7 Hz, 6H, H-17); 7.27-7.21 (t, J=7.2 Hz, 3H, H-18); 3.52-3.45 (t, J$^3$=6.7 Hz, 2H, H-12); 2.99-2.90 (t, 3=6.5 Hz, 2H, H-2); 1.81-1.71 (p, 3=6.8 Hz, 2H, H-11); 1.57-1.48 (p, J$^3$=6.6 Hz, 2H, H-3); 1.41-1.16 (m, 14H, H-4-H-10).

$^{13}$C-NMR (600 MHz, DMSO, 27° C., TMS): δ [ppm]=144.05 (C-15); 128.12 (C-16); 127.75 (C-17); 126.84 (C-18); 85.71 (C-14); 62.83 (C-2); 35.07 (C-12); 32.21 (C-11); 29.26 (C-3); 28.81 (C-7); 28.77 (C-6, C-8); 28.65 (C-5); 28.06 (C-9); 27.47 (C-10); 25.62 (C-4).

ESI-MS: (m/z) calc. for $C_{30}H_{37}BrO$ $(M+H)^+$ 492.2028, ascertained 243.1187 (trityl group) (calc. 243.1174).

IR (neat): $\tilde{\nu}$ [cm$^{-1}$]=3059 (C═C—H); 2927 (C—H); 2854 (—$CH_2$—); 1072 (C—O); 705 (R—Ca).

Example 28

Synthesis of diethyl(11-bromoundecyl)phosphonate

According to Baughman, T. W.[18], the diethyl(11-hydroxyundecyl)phosphonate (1.01 g, 3.28 mmol, 1 eq.) obtained above was dissolved in DCM (10 mL, 157 mmol, 47.9 eq.) in an ice bath, mixed with $PPh_3$ (945 mg, 3.6 mmol, 1.1 eq.) and slowly mixed with $CBr_4$ (1.195 g, 3.6 mmol, 1.1 eq.) while stirring. After 30 minutes, the ice bath was removed and the mixture continued to be stirred for two and a half hours. The reaction solution was controlled by NMR after micro-preparation (80 μL), after which a 1:1 mixture of educt and product was present in the reaction solution. While the reaction was continued at 40° C. for two hours, the product could be detected by ESI-MS using the characteristic isotope pattern. Due to the low solubility of the product in Hex, the residue obtained after evaporation of the reaction solution was triturated with hot Hex (5×100 mL) and the supernatant was concentrated to dryness. Column chromatography (100 mL FS, 50 g KG) [400 mL Hex:EtOAc 4:1, 200 mL Hex:EtOAc 7:3, 200 mL Hex:EtOAc 3:2, 500 mL Hex:EtOAc 1:1] produced the desired product as yellowish oil in 58% yield.

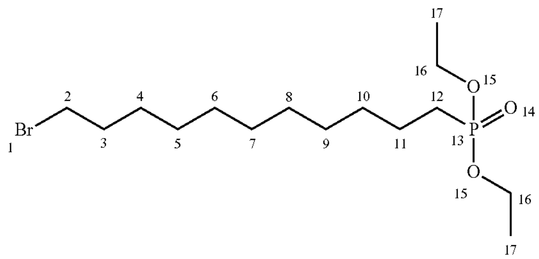

$^1$H-NMR (600 MHz, $CDCl_3$, 27° C., TMS): δ [ppm]=4.13-4.02 (m, 4H, H-16); 3.41-3.37 (t, J$^3$=6.9 Hz, 2H, H-2); 1.87-1.81 (dt, J$^3$=14.6, 6.9 Hz, 2H, H-3); 1.74-1.66 (m, 2H, H-12); 1.62-1.53 (m, 2H, H-11); 1.44-1.21 (m, 6H, H-17; 14H, H-4-H-10).

$^{13}$C-NMR (600 MHz, $CDCl_3$, 27° C., TMS): δ [ppm]=61.52 (C-16); 34.14 (C-2); 32.95 (C-3); 30.77 (C-12), 30.66 (C-11); 29.50 (C-7, C-8); 29.19 (C-6); 28.86 (C-5); 28.28 (C-9); 26.29 (C-10); 25.36 (C-4); 16.61 (C-17).

$^{31}$P-NMR (600 MHz, $CDCl_3$, 27° C., $H_3PO_4$): δ [ppm]=32.65 (P-13).

ESI-MS: (m/z) calc. for $C_{15}H_{32}BrO_3P$ $(M+H)^+$ 370.1272, ascertained 371.1270.

IR (neat): $\tilde{\nu}$ [$cm^{-1}$]=2926 (C—H); 2854 (—$CH_2$—); 1244 ($R(R'O)_2P$═O); 1060 (C—O); 1029 (C—O); 960 (P—O—$C_2H_5$).

Example 29

Synthesis of diethyl(11-bromoundecyl)phosphonate from 1,11-dibromoundecane

According to Tisato, F.[19], 1,11-dibromoundecane (5.24 mL, 16.4 mmol, 4 eq.) was dissolved in $P(OEt)_3$ (716 μL, 4.09 mmol, 1 eq.) and reacted at 200° C. under reflux for two hours. The released ethyl bromide was retained by a dry pipe loaded with activated carbon. The reaction was controlled by DC and NMR.

For purification, the more volatile educt was distilled off at 150° C. in vacuum (0.1 mbar) with a 15 cm Vigreux column for two hours. The $^1$H-NMR spectra showed 9.6% product in the distillate and 14% educt in the sump. The remaining reaction mixture was purified by column chromatography (100 mL FS; 50 g KG) with a step gradient of 10% with 200 mL each [Hex/Hex:EtOAc 3:7].

The $^1$H-NMR spectrum was consistent with the target structure. The product was obtained as turbid oil with 90% yield.

Example 30

Synthesis of diethyl(11-(dimethylamino)undecyl)phosphonate

Diethyl(11-bromoundecyl)phosphonate (440 mg, 1.185 mmol, 1 eq.) was dissolved in a 5.6 M solution of dimethylamine ($NMe_2$) in absolute ethanol [$EtOH_{abs.}$] (2.16 mL, 11.85 mmol, 10 eq.) and stirred at 60° C. for two hours in MW. The reaction was monitored by DC in 98:2 DCM: MeOH.

Solvent and $NMe_2$ were removed from the reaction solution in an oil pump vacuum, the reaction solution was suspended in MTBE (10 mL) and extracted with NaOH 1 M (5 mL) to transfer the hydrobromide formed into the free base. The organic phase was dried with $Na_2SO_4$ and concentrated to dryness. The product was obtained as colorless oil in 91% yield.

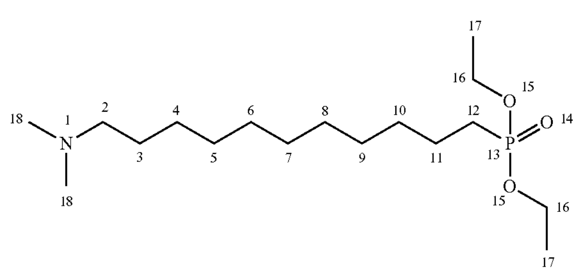

$^1$H-NMR (500 MHz, $CDCl_3$, 27° C., TMS): δ [ppm]=4.16-4.00 (m, 4H, H-16); 2.34-2.18 (m, 2H, H-2; 6H, H-18); 1.74-1.66 (m, 2H, H-12); 1.64-1.51 (m, 2H, H-3); 1.51-1.41 (m, 2H, H-11); 1.39-1.16 (m, 6H, H-17; 14H, H-4-H-10).

$^{13}$C-NMR (500 MHz, $CDCl_3$, 27° C., TMS): δ [ppm]=61.49 (C-16); 59.96 (C-2); 45.45 (C-18); 30.81 (C-12); 30.68 (C-11); 29.65 (C-7, C-8); 29.48 (C-3); 29.21 (C-6); 27.65 (C-5); 27.57 (C-9); 26.39 (C-10); 25.27 (C-4); 16.62 (C-17).

ESI-MS: (m/z) calc. for $C_{17}H_{38}NO_3P$ $(M+H)^+$ 335.2589, ascertained 336.2672.

IR (neat): $\tilde{\nu}$ [$cm^{-1}$]=3423 (N—H); 2981 (C—H); 2927 (C—H); 2855 (—$CH_2$—); 1231 ($R(R'O)_2P$═O); 1065 (C—O); 1027 (C—O); 963 (P—O—$C_2H_5$).

Example 31

Synthesis of 3-((11-(diethoxyphosphoryl)undecyl) dimethylammonio)-propane-1-sulfonate Diethyl(11-(dimethylamino)undecyl)phosphonate (300 mg, 894 μmol, 1 eq.) was dissolved in dry $CHCl_3$ (6 mL 83.8 eq.), 1,3-propane sultone (83 μL, 921 μmol, 1.03 eq.) was added and stirred at 100° C. in an MW furnace for two hours.

The product was precipitated with 6:1 MTBE:EtOAc (40 mL), separated by centrifugation, suspended in pure EtOAc (40 mL), centrifuged again and dissolved in $H_2O$ (10 mL). Lyophilization yielded a hygroscopic solid in 59% yield.

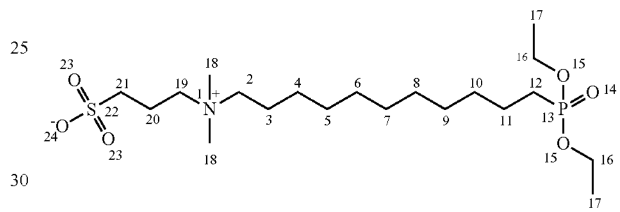

$^1$H-NMR (400 MHz, $D_2O$, 27° C., TMS): δ [ppm]=4.22-4.11 (pd, 3=7.1, 2.3 Hz, 4H, H-16);

3.53-3.46 (m, 2H, H-21); 3.39-3.31 (m, 2H, H-19); 3.17-3.09 (s, 6H, H-18); 3.05-2.99 (t, $J^3$=7.2 Hz, 2H, H-2), 2.30-2.20 (m, 2H, H-20); 1.98-1.87 (m, 2H, H-12); 1.85-1.75 (m, 2H, H-3); 1.68-1.55 (m, 2H, H-11); 1.49-1.30 (m, 6H, H-17; 14H, H-4-H-10).

$^{13}$C-NMR (400 MHz, $D_2O$, 27° C., TMS): δ [ppm]=64.37 (C-2); 63.10 (C-16); 62.07 (C-19); 50.58 (C-21); 47.31 (C-18); 29.50 (C-12); 28.56 (C-11); 28.47 (C-7, C-8); 28.17 (C-20); 25.49 (C-3); 24.35 (C-6); 23.00 (C-5); 21.83 (C-9); 21.42 (C-10); 18.17 (C-4); 15.64 (C-17).

$^{31}$P-NMR (400 MHz, $D_2O$, 27° C., $H_3PO_4$): δ [ppm]=31.94 (P-13).

ESI-MS: (m/z) calc. for C20H44NO6PS (M+H)+ 457.2627, ascertained 458.2713.

IR (neat): $\tilde{\nu}$ [$cm^{-1}$]=3313 ($R_2R'R''N+$); 2504 ($R_2R'R''N+$); 1636 ($R(R'O)_2P$═O); 1457 (—O—$CH_2$—); 1045 (S═O); 589 ($R(R'O)_2P$═O); 589 (C—C).

Example 32

Synthesis of 3-(dimethyl(11-phosphonoundecyl) ammonio)propane-1-sulfonate

A 23 mM solution of 3-((11-(diethoxyphosphoryl)undecyl)dimethylammonio)-propane-1-sulfonate (104 mg, 227 μmol) in Millipore-$H_2O$ was hydrolyzed under microwave heating at 250° C. and a pressure of about 40 bar for one hour. Lyophilization produced a white solid which, according to the $^1$H-NMR spectrum, corresponded to the desired product in 94% yield.

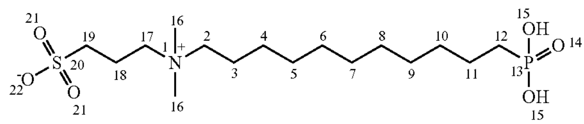

$^1$H-NMR (400 MHz, $D_2O$, 27° C., TMS): δ [ppm]=3.53-3.46 (m, 2H, H-19); 3.39-3.31 (m, 2H, H-17); 3.17-3.09 (s, 6H, H-16); 3.03-2.97 (t, $J^3$=7.2 Hz, 2H, H-2), 2.34-2.15 (m, 2H, H-20); 1.88-1.70 (dt, $J^3$=17.2, 8.2 Hz, 4H, H-3, H-12); 1.67-1.51 (m, 2H, H-11); 1.48-1.27 (m, 14H, H-4-H-10).

$^{13}$C-NMR (400 MHz, $D_2O$, 27° C., TMS): δ [ppm]=64.39 (C-2); 62.06 (C-17); 50.55 (C-19); 47.30 (C-16); 29.79 (C-12); 29.63 (C-11); 28.48 (C-7, C-8); 28.10 (C-18); 26.96 (C-3); 25.64 (C-6); 25.41 (C-5); 22.08 (C-9); 21.78 (C-10); 18.15 (C-4).

$^{31}$P-NMR (400 MHz, $D_2O$, 27° C., $H_3PO_4$): δ [ppm]=32.14 (P-13).

ESI-MS: (m/z) calc. for $C_{16}H_{36}NO_6PS$ $(M+H)^+$ calc. 401.2001, ascertained 402.2077.

IR (neat): $\tilde{\nu}$ [$cm^{-1}$]=2915 (C—H); 2849 (—$CH_2$—); 2291 ($R_2R'R''N+$); 1653 ($R(HO)_2P$═O); 1467 (C—H); 1219 (—$SO_3$—); 1149 (—$SO_3$—); 1034 (C—N); 974 (C—C); 940 (P—O); 768 (C—C); 730 (C—C); 521 (C—C); 491 (C—C); 422 ($R(HO)_2P$═O).

Example 33

Synthesis of (11-(dimethylamino)undecyl)phosphonic acid

A 23 mM solution of diethyl(11-(dimethylamino)undecyl)phosphonate (100 mg, 298 μmol) in millipore-$H_2O$ was reacted under microwave heating at 250° C. and a pressure of about 40 bar[53] for one hour. Lyophilization resulted in a white solid which, according to the $^1$H-NMR spectrum, corresponded to the desired product in 94% yield.

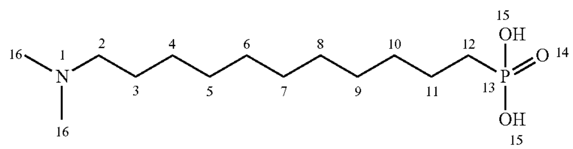

$^1$H-NMR (400 MHz, $D_2O$, 27° C., TMS): δ [ppm]=3.43-3.35 (q, $J^3$=7.3 Hz, 2H, H-2); 3.32-3.24 (m, 2H, H-15); 3.09-3.00 (s, 6H, H-16); 1.84-1.69 (m, 2H, H-12); 1.69-1.48 (m, 4H, H-3, H-11); 1.46-1.26 (m, 14H, H-4-H-10).

$^{13}$C-NMR (400 MHz, $D_2O$, 27° C., TMS): δ [ppm]=60.31 (C-2); 42.50 (C-16); 38.93 (C-12); 30.51 (C-11); 30.34 (C-8); 28.93 (C-7); 28.52 (C-3); 28.34 (C-6); 28.08 (C-5); 27.62 (C-9); 26.74 (C-10); 25.43 (C-4).

$^{31}$P-NMR (400 MHz, $D_2O$, 27° C., $H_3PO_4$): δ [ppm]=27.74 (P-13).

ESI-MS: (m/z) calc. for $C_{13}H_{30}NO_3P$ ((M+H)+279.1963, ascertained 280.2091.

IR (neat): $\tilde{\nu}$ [cm]=3399 (N—H); 2919 (C—H); 2850 (—$CH_2$—); 2345 ($R(HO)_2P$═O); 1576 (C—N); 1416 (C—H); 1220 ($R(R'O)_2P$═O); 1158 (C—N), 1035 (S═O), 892 (P—O), 780 (C—C), 470 (C—C).

REFERENCES

[1] Carambia, A.; Freund, B.; Schwinge, D.; Bruns, O. T.; Salmen, S. C.; Ittrich, H.; Reimer, R.; Heine, M.; Huber, S.; Waurisch, C.; et al. Nanoparticle-Based Autoantigen Delivery to Treg-Inducing Liver Sinusoidal Endothelial Cells Enables Control of Autoimmunity in Mice. *J. Hepatol.* 2015, 62, 1349-1356.

[2] Carambia, A.; Freund, B.; Schwinge, D.; Heine, M.; Laschtowitz, A.; Huber, S.; Wraith, D. C.; Korn, T.; Schramm, C.; Lohse, A. W.; et al. TGF-β-Dependent Induction of CD4⁺CD25⁺Foxp3⁺ Tregs by Liver Sinusoidal Endothelial Cells. *J. Hepatol.* 2014, 61, 594-599.

[3] Longmire, M. R.; Ogawa, M.; Choyke, P. L.; Kobayashi, H. Biologically Optimized Nanosized Molecules and Particles: More Than Just Size. *Bioconjug. Chem.* 2011, 22, 993-1000.

[4] Petros, R. A.; DeSimone, J. M. Strategies in the Design of Nanoparticles for Therapeutic Applications. *Nat. Rev. Drug Discov.* 2010, 9, 615-627.

[5] Schipper, M. L.; Iyer, G.; Koh, A. L.; Cheng, Z.; Ebenstein, Y.; Aharoni, A.; Keren, S.; Bentolila, L. A.; Li, J.; Rao, J.; et al. Particle Size, Surface Coating, and PEGylation Influence the Biodistribution of Quantum Dots in Living Mice. *Small* 2009, 5, 126-134.

[6] Fischer, H. C.; Liu, L.; Pang, K. S.; Chan, W. C. W. Pharmacokinetics of Nanoscale Quantum Dots: In Vivo Distribution, Sequestration, and Clearance in the Rat. *Adv. Funct. Mater.* 2006, 16, 1299-1305.

[7] Ilium, L.; Davis, S. S.; Wilson, C. G.; Thomas, N. W.; Frier, M.; Hardy, J. G. Blood Clearance and Organ Deposition of Intravenously Administered Colloidal Particles. The Effects of Particle Size, Nature and Shape. *Int. J. Pharm.* 1982, 12, 135-146.

[8] Carambia, A.; Freund, B.; Schwinge, D.; Bruns, O. T.; Salmen, S. C.; Ittrich, H.; Reimer, R.; Heine, M.; Huber, S.; Waurisch, C.; et al. Nanoparticle-Based Autoantigen Delivery to Treg-Inducing Liver Sinusoidal Endothelial Cells Enables Control of Autoimmunity in Mice. *J. Hepatol.* 2015, 62, 1349-1356.

[9] Sørensen, K. K.; McCourt, P.; Berg, T.; Crossley, C.; Le Couteur, D.; Wake, K.; Smedsrod, B. The Scavenger Endothelial Cell—A New Player in Homeostasis and Immunity. *Am. J. Physiol. Regul. Integr. Comp. Physiol.* 2012, 303, R1217-R1230.

[10] Kamimoto, M.; Rung-Ruangkijkrai, T.; Iwanaga, T. Uptake Ability of Hepatic Sinusoidal Endothelial Cells and Enhancement by Lipopolysaccharide. *Biomed. Res.* 2005, 26, 99-107.

[11] Carambia, A.; Freund, B.; Schwinge, D.; Heine, M.; Laschtowitz, A.; Huber, S.;
Wraith, D. C.; Korn, T.; Schramm, C.; Lohse, A. W.; et al. TGF-β-Dependent Induction of CD4⁺CD25⁺Foxp3⁺ Tregs by Liver Sinusoidal Endothelial Cells. *J. Hepatol.* 2014, 61, 594-599.

[12] Yang, C.; Liu, H.; Zhang, Y.; Zhigang, X.; Wang, Y.; Cao, B.; Wang, M. *Biomacromolecules,* 2016, 17, 1673-1683.

[13] Pérez-Balado, C.; Nebbioso, A.; Rodriguez-Graña, P.; Minichiello, A.; Miceli, M.; Altucci, L.; de Lera, Á. R. *J. Med. Chem.,* 2007, 50, 2497-2505.

[14] Minet, I.; Delhalle, J.; Hevesi, L.; Mekhalif, Z. *J. Colloid Interface Sci.,* 2009, 332, 2, 317-326.

[15] Lai, C.; Xi, C.; Chen, W.; Hua, R. *Tetrahedron,* 2006, 62, 6295-6302.

[16] Azzouz, R.; Bischoff, L.; Fouquet, M.-H.; Marsais, F. *Synlett,* 2005, 2808.

[17] Rele, S.; Nayak S. K. *Synthetic Communications,* 2002, 32, 22, 3533-3540.

[18] Baughman, T. W.; Sworen, J. C.; Wagener, K. B. *Tetrahedron,* 2004, 60, 10943-10948.

[19] Nihon Medi-Physics Co., Ltd., 2007, *Intermediate compound of technetium nitride complex for radiodiagnostic imaging*, Inventor: Tisato, F.; Refosco, F.; Bolzati, C.; et al., JP, Patent Document: PCT/JP2006/301260.

The invention claimed is:

1. A method of decreasing immunological responses comprising administering to a patient in need thereof a zwitterionic nanoparticle, wherein the zwitterionic nanoparticle comprises at least one nanoparticle and a zwitterionic case comprising a long chain zwitterionic ligand, which case encloses the nanoparticle;

wherein the zwitterionic ligand is described by the formula:

$$A\text{-}X\text{—}[L^1\text{-}Z^1\text{-}L^2\text{-}Z^2]_n$$

wherein A is optionally a group having affinity for a surface of the nanoparticle or is an at least divalent atom capable of forming a covalent bond to the nanoparticle;

$L^1$ and $L^2$ are mutually independent linker groups;

X is an optional branching element such that X has, in addition to the bond to A, at least one further bond to $L^1$;

n comprises the integers between 1 and a maximum valence of X-1;

$Z^1$ includes a first charged or ionizable group; and $Z^2$ includes a second charged or ionizable group, provided that they are opposite in case $Z^1$ or $Z^2$ carry charges; and wherein decreasing immunological responses comprises reduction of auto-aggressive inflammations or suppression of an autoimmune disease.

2. The method according to claim 1, wherein decreasing immunological responses comprises a decrease of an allergy response or a suppression of immunological responses against biologicals.

3. The method of claim 1, wherein the nanoparticles are coupled with autoantigen peptides.

4. The method of claim 3, wherein the autoantigen peptide is myelin basic protein.

5. The method of claim 1, wherein the zwitterionic nanoparticle is not taken up by Kupffer cells.

6. The method of claim 1, wherein the zwitterionic nanoparticle is absorbed into liver sinusoidal endothelial cells.

7. The method according to claim 1, wherein the nanoparticle is one or more of a luminescent, magnetic, and plasmonic nanoparticle.

8. The method according to claim 1, wherein the nanoparticle contains at least one active substance molecule.

9. The method according to claim 1, wherein the nanoparticle is a semiconductor nanoparticle.

10. The method according to claim 9, wherein the nanoparticle is doped with heavy metal ions including one of Ag, Cu, Co and Mn.

11. The method according to claim 1, wherein the nanoparticle is a lanthanide-doped nanoparticles having host lattices.

12. The method according to claim 1, wherein the nanoparticle is a metallic nanoparticle or consists of a metal oxide.

13. The method according to claim 1, wherein a structure of the nanoparticle is described by the formula $M_W N_X A_y B_Z$, wherein M and N are independently selected from elements of groups 8, 9, 10, 11, 12, 13 or 14 of a Periodic Table of Elements, including one of Fe, Co, Ni, Pt, Cu, Zn, Cd, Al, Ga, In, Ge, Sn, and Pb, and wherein A and B are independently selected from the elements 10, 11, 13, 15 or 16 of the Periodic Table of the Elements, including one of Pd, Pt, N, P, As, Sb, Ga, 0, S, Se, and Te, and wherein w, x, y and z can independently attain integer multiples of a value between 0 and 1, provided that a total positive charge of cationic elements in the nanoparticle is opposite and equal to a negative charge of anionic elements of the nanoparticle.

14. The method according to claim 13, wherein the nanoparticle is surrounded by at least one shell.

15. The method according to claim 14, wherein a composition of the shell includes $O_s C_t D_u$, wherein 0 is independently selected from elements of groups 8, 9, 10, 11, 12, 13 or 14 of the Periodic Table of the Elements, including Fe, Co, Ni, Pt, Cu, Zn, Cd, Al, Ga, In, Ge, Sn, and Pb, and C and D are independently selected from the elements 10, 11, 15 or 16 of the Periodic Table of the Elements, including Pd, Pt, N, P, As, Sb, 0, S, Se, and Te, and wherein s, t, and u can independently attain integer multiples of a value between 0 and 1, provided that the total positive charge of cationic elements is opposite and equal to the negative charge of the anionic elements and that the compositions of $M_W N_X A_y B_Z$ and $O_s C_t D_u$ are different.

16. The method according to claim 1, wherein A is selected from the group consisting of C, N, O, S, P or Si, wherein at least one amino, mercapto, dithiocarbamate, carboxy, phosphate, phosphonate group is provided.

17. The method according to claim 1, wherein $L^1$ and $L^2$ are mutually independent linear or branched, optionally saturated or unsaturated hydrocarbon chains having one to forty carbon atoms, optionally containing heteroatoms from the group consisting of N, O, P, Si and S.

* * * * *